(12) United States Patent
Mardi et al.

(10) Patent No.: US 9,283,199 B2
(45) Date of Patent: Mar. 15, 2016

(54) HALOGENATED ALIPHATIC CARBOXYLIC ACIDS, OLIGOMERS AND/OR POLYMERS THEREOF AND THEIR USE IN DEVITALIZING EXTERNAL AND INTERNAL NEOPLASMS

(75) Inventors: Shalva Mardi, Binningen (CH); Rosa Mardi, Binningen (CH); Gymsher Mardi, Binningen (CH); Laura Mardi, Binningen (CH); Shimon Slavin, Tel-Aviv (IL)

(73) Assignee: Cimas Limited, Nicosia (CY)

( * ) Notice: Subject to any disclaimer, the term of this patent is extended or adjusted under 35 U.S.C. 154(b) by 267 days.

(21) Appl. No.: 12/796,804

(22) Filed: Jun. 9, 2010

(65) Prior Publication Data

US 2011/0052641 A1 Mar. 3, 2011

Related U.S. Application Data

(60) Provisional application No. 61/185,226, filed on Jun. 9, 2009.

(51) Int. Cl.

| | | |
|---|---|---|
| *A61K 31/19* | (2006.01) | |
| *A61K 31/194* | (2006.01) | |
| *A61K 31/22* | (2006.01) | |
| *C07C 59/315* | (2006.01) | |
| *C07C 69/63* | (2006.01) | |
| *C07C 69/708* | (2006.01) | |

(52) U.S. Cl.
CPC ............... *A61K 31/19* (2013.01); *A61K 31/194* (2013.01); *A61K 31/22* (2013.01); *C07C 59/315* (2013.01); *C07C 69/63* (2013.01); *C07C 69/708* (2013.01)

(58) Field of Classification Search
CPC ............................. A61K 31/19; A61K 31/194
See application file for complete search history.

(56) References Cited

U.S. PATENT DOCUMENTS

| | | | |
|---|---|---|---|
| 2,734,075 A | 2/1956 | Brust et al. | |
| 4,624,851 A | 11/1986 | Revici | |
| 4,824,955 A * | 4/1989 | Ekimoto et al. | 546/266 |
| 6,071,919 A * | 6/2000 | Theodore et al. | 514/252.12 |
| 2002/0173472 A1 | 11/2002 | Pezzuto et al. | |
| 2003/0143165 A1 | 7/2003 | Evans et al. | |
| 2006/0041019 A1 | 2/2006 | Nagato et al. | |
| 2006/0135618 A1 | 6/2006 | Jean et al. | |
| 2006/0160897 A1 | 7/2006 | Pelicci et al. | |
| 2007/0128154 A1 | 6/2007 | Hadba et al. | |
| 2007/0149618 A1 | 6/2007 | Cuevas Sanchez et al. | |
| 2008/0187511 A1 | 8/2008 | Shurin et al. | |

FOREIGN PATENT DOCUMENTS

| | | |
|---|---|---|
| DE | 4407484 | 6/1995 |
| EP | 1293498 | 3/2003 |
| EP | 1746082 | 1/2007 |
| JP | 09-227388 | 9/1997 |
| JP | 10-130153 | 5/1998 |
| RU | 2261243 | 9/2005 |
| RU | 2007132295 | 3/2009 |
| RU | 2007138450 | 4/2009 |
| RU | 2366648 | 9/2009 |
| WO | WO 95/11699 | 5/1995 |
| WO | WO 2004/019927 | 3/2004 |
| WO | WO 2006/024491 | 3/2006 |
| WO | WO 2006/042062 | 4/2006 |
| WO | WO 2006/108276 | 10/2006 |
| WO | WO 2010/143188 | 12/2010 |

OTHER PUBLICATIONS

Peckham et al 'Oxford Textbook of Oncology' Oxford University Press, vol. 1, p. 451, 1995.*
Office Action Dated Nov. 30, 2010 From the Ministerio de Comercio e Industrias de Panama Re. Application No. 88794 and Its Summary Into English.
Response Dated May 26, 2011 to Office Action of Nov. 30, 2010 From the Ministerio de Comercio e Industrias de Panama Re. Application No. 88794.
Examination Report Dated Oct. 17, 2011 From the Ministerio de Comercio e Industrias, Direccion General del Registro de la Propriedad Industrial de la Republica de Panama Re. Application No. 88794-01 and Its Summary in English.
Communication Relating to the Results of the Partial International Search Dated Jan. 20, 2011 From the International Searching Authority Re. Application No. PCT/IL2010/000455.
Orchard et al. "Substrate Specificity of the Short Chain Fatty Acyl-Coenzyme A Synthetase of Pinus Radiata", Phytochemistry, XP002614816, 41(6): 1465-1472, 1996. Table 2, p. 1471, 1-h Col., § 3.
International Search Report and the Written Opinion Dated Mar. 14, 2010 From the Internaional Searching Authority Re. Application No. PCT/IL2010/000455.
Kim et al. "Preparation of α,ω-Ditriazinylperfluoroalkane Derivatives (1)", Journal of Heterocyclic Chemistry, XP002625857, 11(4): 563-568, Aug. 1, 1974. Compounds IIIa, IIIb.
Lo et al. "Rhenium(VII) Oxide Catalyzed Heteroacylative Ring-Opening Dimerizalion of Tetrahydrofuran", Journal of the American Chemical Society, JACS, XP002625858, 129(5): 1246-1253, Feb. 2007. Abstract, Table 1.
Mardi et al. "Novel Paharmaceutical Compound (Mc-Mardil) as the Immunomodulator and Universal Devitalisator of Neoplasmas in the Treatment of External and Internal Tumour Growths", International Journal of Immunorchabilitation, XP008126021, 11(2): 181-183, Oct. 20, 2009.

(Continued)

Primary Examiner — Wu-Cheng Winston Shen
Assistant Examiner — Christopher R Stone

(57) ABSTRACT

Halogenated aliphatic carboxylic acids, salts and/or oligomers or polymers thereof, which exhibit a devitalizing effect of neoplastic tissues, are disclosed. Methods and uses that utilize these compounds for the treatment of medical conditions associated with a neoplastic tissue are also disclosed. Further disclosed are methods and uses that utilize these compounds for reducing or abolishing blood and lymph as well local dissemination of malignant neoplastic cells during a surgical removal thereof, thereby preventing recurrences and distance metastases, and/or inducing immune response to potentially malignant, pre-malignant and/or malignant cells. Further disclosed are novel oligomeric forms of halogenated aliphatic carboxylic acids, pharmaceutical compositions containing same and uses thereof.

14 Claims, 3 Drawing Sheets
(2 of 3 Drawing Sheet(s) Filed in Color)

(56) References Cited

OTHER PUBLICATIONS

Ruddock et al. "The Reactions of Palladium(II), Thallium(III) and Lead(IV) Trifluoroacetates With 3β-Acetoxyandrost-5-En-17-One: Crystal Structure of the First Trifluoroacetate Bridged 5,6,7-π-Allyl Steroid Palladium Dimer", Steroids, XP004502567, 69(3): 193-199, Mar. 1, 2004. p. 195, 1-h Col., § 2-3, Compound 20.
Willgerodt et al. "Beiträge zur Kenntniss des Acetonchloroforms, Chlorisobuttersäuretrichlorids and des Acetonchloroformäthers", Journal für Praktische Chemie, XP002625859, 41(1): 515-526, Mar. 1890. P.515, § 1—p. 518, Last §.
Epple et al. "Oligomerization and Polymerization in Sodium Salts of Chlorocarboxylic Acids", Liebigs Annalen, 1997(1): 81-85, Jan. 27, 2006. Abstract.
Foy "Absorption, Distribution, & Metabolism of 2,2-Dichloropropionic Acid in Relation to Phytotoxicity. T. Penetration & Translocation of C136- and C14-Labeled Dalapon", Plant Physiology, 36(5): 688-697, 1961.
Foy "Absorption, Distribution, & Metabolism of 2,2-Dichloropropionic Acid in Relation to Phytotoxicity. II. Distribution & Metabolic Fate of Dalapon in Plants", Plant Physiology, 36(5): 698-706, 1961.
Marchesi et al. "Comparing the Dehalogenase Gene Pool in Cultivated α-Halocarboxylic Acid-Degrading Bacteria With the Environmental Metagene Pool", Applied and Environmental Microbiology, 69(8): 4375-4382, Aug. 2003.
Marchesi et al. "Diversity of α-Halocarboxylic Acid Dehalogenases in Bacteria Isolated From a Pristine Soil After Enrichment and Selection on the Herbicide 2,2-Dichloropropionic Acid (Dalapon)", Environmental Microbiology, 5(1): 48-54, 2003.
Mardi et al. "Selenium Compound for the Treatment of Viral, Benign, Premalignant and Nonmetastasizing Malignant Lesions of the Skin and Visible Mucuos Membrane", International Journal of Immunorehabilitation, 3(2): 23-31, 2001.
Mayeux et al. "The Effect of 2,3,6-Trichlorophenylacetic and 2,2-Dichloropropionic Acids on Nitrite Oxidation", Applied Microbiology, 10: 206-210, 1962.
Tong et al. "Glutathione Transferase Zeta-Catalyzed Biotransformation of Dichloroacetic Acid and Other α-Haloacids", Chemical Research in Toxicology, 11(11): 1332-1338, 1998.
Written Opinion and Search Report Dated Nov. 2, 2012 From the Intellectual Property Office of Singapore Re. Application No. 201108928-1.
Examination Report Dated Sep. 28, 2012 From the Intellectual Property Office of New Zealand Re. Application No. 596781.
Communication Pursuant to Article 94(3) EPC Dated Jun. 5, 2013 From the European Patent Office Re. Application No. 10731814.9.
Office Action Dated Apr. 1, 2013 From the State Intellectual Property Office of the People's Republic of China Re. Application No. 201080034338.9 and Its Summary and English Translation of Text.
Translation of Search Report Dated Apr. 1, 2013 From the State Intellectual Property Office of the People's Republic of China Re. Application No. 201080034338.9.
Notification of Patentability of the Invention Dated May 14, 2013 From the Eurasian Patent Organization, The Eurasian Patent Office Re. Application No. 201270016 and Its Translation Into English.
Decision of Rejection Dated Dec. 16, 2014 From the Japanese Patent Office Re. Application No. 2012-514593 and Its Machine Translation Into English.
Written Opinion and Search Report Dated Jan. 16, 2014 From the Intellectual Property Office of Singapore Issued by the Danish Patent and Trademark Office Re. Application No. 201303311-3.
Office Action Dated Jun. 23, 2014 From the Israel Patent Office Re. Application No. 216870 and Its Translation Into English.
Communication Pursuant to Article 94(3) EPC Dated Nov. 20, 2014 From the European Patent Office Re. Application No. 10731814.9.
Communication Pursuant to Article 94(3) EPC Dated Jan. 21, 2014 From the European Patent Office Re. Application No. 10731814.9.
Requisition by the Examiner Dated Jun. 4, 2015 From the Canadian Intellectual Property Office Re. Application No. 2,763,862.
Communication Pursuant to Article 94(3) EPC Dated Jun. 16, 2014 From the European Patent Office Re. Application No. 10731814.9.
Notice of Reason for Rejection Dated Jun. 27, 2014 From the Japanese Patent Office Re. Application No. 2012-514593 and Its Translation Into English.

\* cited by examiner

HALOGENATED ALIPHATIC CARBOXYLIC ACIDS, OLIGOMERS AND/OR POLYMERS THEREOF AND THEIR USE IN DEVITALIZING EXTERNAL AND INTERNAL NEOPLASMS

RELATED APPLICATION/S

This application claims the benefit of priority under 35 USC 119(e) of U.S. Provisional Patent Application No. 61/185,226 filed Jun. 9, 2009, the contents of which are incorporated herein by reference in their entirety.

FIELD AND BACKGROUND OF THE INVENTION

The present invention, in some embodiments thereof, relates to compounds, compositions and methods for treating disorders associated with pathological hyperplasia, metaplasia, dysplasia and neoplasia (oncoplasia) tissues, such as, for example, skin and visible mucosal tumors and lesions and internal neoplasms.

Neoplasia is a general term used to describe abnormal proliferation of cells (such as malignant neoplasia). This abnormal proliferation may be a result of many disorders (such as a viral infection or cancerogenesis) and usually causes a lump or tumor. Neoplastic tissue may be characterized as being viral, benign, pre-malignant or malignant.

Cell proliferation is regulated by a balance between growth-promoting proto-oncogenes and growth-constraining tumor-suppressor genes. Oncogenesis can be caused by genetic alterations to the genome that result in the mutation of those cellular elements that govern the interpretation of cellular signals, such as potentiation of proto-oncogene activity or inactivation of tumor suppression. It is believed that the interpretation of these signals ultimately influences the growth and differentiation of a cell, and that misinterpretation of these signals can result in neoplastic growth (neoplasia).

Current methods of treating neoplasia include surgery, laser surgery, photodynamic therapy, cryotherapy, chemotherapy and radiation. Chemotherapy involves administration of compounds having antitumor activity, such as alkylating agents, antimetabolites and antitumor antibiotics. The efficacy of chemotherapy is often limited by severe side effects, including nausea and vomiting, bone marrow depression, renal damage and central nervous system depression.

Radiation therapy (radiotherapy) relies on the greater ability of normal cells, in contrast to neoplastic cells, to repair themselves after treatment with radiation. Radiotherapy, however, is limited by possible sensitivity of the tissue surrounding the tumor and further by development of resistance thereto.

Surgery involves the bulk removal of diseased (e.g., neoplastic) tissue. When tumor growth is recognized, excision of the tumor mass by surgery is regarded as the therapy of choice. However, during the surgical manipulation, dissemination of malignant tumor cells into the blood and lymph vessels may occur, resulting in metastasis to other body locations and postoperative recurrence resulting in a poor prognosis.

The skin is the largest organ of the body, covering the entire exterior of the body, and includes the epidermis, dermis and subcutaneous layers. Numerous disorders of the skin are known, ranging from those which merely cause discomfort or psychological stress, such as rashes, through benign or cancerous skin lesions, to life-threatening conditions such as skin cancer.

With the increase in the world's ageing population there is a concomitant increase in occurrence of skin disorders that are characterized by skin neoplasia, such as skin lesions and skin cancer, which are often caused by extensive exposure of the skin to ultraviolet beta rays and chemicals in various cosmetic and skin care products. There are several types of skin cancers, the most common being basal cell carcinoma and squamous cell carcinoma, which are both non-melanoma skin cancers.

Basel cell carcinoma develops from abnormal growth of the cells in the lowest layer of the epidermis. Squamous cell cancer involves changes in the squamous cells, found in the middle layer of the epidermis. Malignant melanoma, which occurs in the melanocytes, is less common than squamous or basal cell carcinoma but is much more dangerous. Melanoma is the leading cause of death from skin malignant disease.

Actinic keratosis is a skin condition that sometimes develops into squamous cell carcinoma. Actinic keratosis (also known as a solar keratosis) is a precancerous skin growth usually caused by sun exposure. The most common sites for these lesions are the face, ears, scalp, neck, forearms and hands. Actinic cheilitis is a form of labial mucosa actinic keratosis which occurs on the lips and causes them to become dry, cracked, scaly and pale or white.

Leukoplakia, representing another precursor condition, is manifested by white patches on the tongue or inside the mouth, which have the potential to develop into squamous cell carcinoma.

Benign (non-cancerous) skin tumors may be present at birth, be genetic or develop later. Some benign skin tumors are known to be caused by viruses (for example, warts), systemic disease (for example, xanthelasmas or xanthomas caused by excess cholesterol and fats in the blood), and environmental factors (for example, moles (nevi) and epidermal cysts stimulated by sunlight). Other examples of benign skin tumors are dermatofibromas; angiomas (such as hemangiomas, port-wine stains, lymphangiomas, and pyogenic granulomas); seborrheic keratoses; and acrochordons, or skin tags.

Keratoacanthomas are rapidly growing lesions that occur primarily on sun-exposed skin in older persons. Keratoacanthomas are usually solitary, but multiple lesions may be present. Possible causative agents include ultraviolet light, human papilloma virus, and prolonged contact with coal tar derivatives.

The standard therapy used in benign, pre-malignant and malignant skin tumors is determined by many factors, including the exact hislologic subtype, the tumor size, the growth characteristics and the anatomic location. Treatment is also determined by the previous treatment received, current medical problems and patient's expectations.

Treatment options may be categorized as surgical and non-surgical. Surgical treatments include laser or electrodessication and curettage, simple or wide local excision of the lesion or Mohs micrographic surgery. Non-surgical treatments include radiation therapy, photodynamic therapy, cryotherapy and topical drug therapy.

A surgical treatment of benign, pre-malignant and malignant skin tumors might not be applicable in all patients. The aggressiveness nature of the surgical techniques (as compared to non-surgical procedures) may lead, in some cases, to severe disfigurement due to bony involvement, loss of vision (in cases of tumors located near the eyes) and even death.

Surgical treatment is particularly problematic in treating skin tumors located near the eyes or in the nose region as well as in treating patients suffering from multiple tumors and reoccurrences.

Furthermore, surgical treatment is associated with complications such as bleaching, infections, ulcerations, pain, allergical and exematic reactions, healing problems as well as hypertrophic, kelloidal and painful scars. Such complications often require the administration of additional drugs such as steroids (either topically or systemically), antibiotics, antiseptics, anticoagulants and different kinds of tissue-stimulated creams or drugs, as well as occlusive hydrophilic dressings and laminates (silicon/nylon mesh, collagen, fibrin, etc.).

One of the main concerns when using a surgical procedure for treating skin and mucosal related cancer is the intraoperative dissemination of cancer cells and the subsequent penetration of the cells into blood or lymph vessels. Shedding of cancer cells into the blood and lymph circulation of a patient during surgery is one of the factors of development of post-operative tumor recurrences and distance metastasis associated with a very poor prognosis.

An alternative to surgical treatment is radiation therapy which works by damaging the DNA of cells. Because this therapy is expensive and requires frequent visits over several weeks, it is often not an option for elderly patients with a limited support system. Long term cosmetic results may be poor and the complications of tissue necrosis, chondritis and osteoradionecrosis may occur. Another drawback is the risk of a radiation-induced malignant growth that may occur later, thus radiation is generally not recommended as the primary treatment in patients younger than 50 years of age.

Photodynamic therapy involves the topical administration of photoreactive chemicals and irradiation with light strong enough to activate the chemicals, causing them to emit free radicals and destroy pathologic cells. This therapy is currently limited by its high cost and by persistent skin photosensitivity that lasts weeks.

Cryotherapy is the application of extreme cold to destroy abnormal or diseased tissue. Warts, moles, skin tags, solar keratoses and small skin cancers are candidates for cryosurgical treatment. Disadvantages are the lack of margin control, tissue necrosis, over or under treatment of the tumor, and long recovery time.

Topical drug therapy is limited by superficial basaliomas and actinic keratosis only, to lesions confined to the epidermis. A 5% of 5-fluorouracil (5-FU) cream (Efudex®, Valeant Pharmaceuticals) used in conjugation with topical retinoids may deepen the therapeutic effect and minimize the risk of the disease persisting at the adnexal level but, the treatment is associated with many side effects.

A 5% preparation of Imiquimod cream (Aldara™, 3M Pharmaceuticals), an antiviral agent and as an interferon inducer, applied for 6 weeks has also been shown to eradicate superficial basal cell carcinoma in more than 80% of the cases but the use of imiquimod may be limited by its cost, drug contraindications and side effect. An injection of 5-FU (Adrucil®, Teva Parenteral Medicines, Inc.) or methotrexate Rheumatrex®, DAVA Pharmaceuticals) is primarily limited to lesions whose clinical characteristics and histology are consistent with keratoacanthoma. Intralesional administration of interferon (Roferon-A®, Roche Pharmaceuticals) has been effective for treating basal cell carcinoma but this regimen requires multiple injections for several weeks, is expensive and is associated with flu-like symptoms.

Solcoderm® (Invented by S. Mardi) is an aqueous solution containing organic and inorganic acids in the presence of copper ions. The solution destroys a lesion by tissue mummification. It has been used for the treatment of a variety of benign skin lesions, including solar keratosis, verrucae, condyloma acuminata, hemangiomas and papillomas. The use of Solcoderm in benign skin lesions gives usually good cosmetic results. Solcoderm has also been used in the treatment of malignant lesions including basal and squamous cell carcinoma.

Topical drug treatments of benign, pre-malignant and malignant skin tumors have been also disclosed, for example, in U.S. patent application Ser. Nos. 11/275,258, 11/924,354, 11/506,469, 10/530,723, 10/310,824 and 10/071,124.

Mardi et al. describe a selenium compound of halogenated and polymerized carboxylic acid complex hydrate for treatment of benign, viral, premalignant and malignant non metastasizing pigmented and non-pigmented skin and visible membranous mucosal lesions or tumors [2001; *International journal of Immunorehabilitation* 3:23-31].

2,2-Dichloropropanoic acid ($CH_3$—$CCl_2$—$C(=O)OH$; DPA; Dalaphon; CAS No. 75-99-0) is a chemical widely used as a water disinfectant and is also used as an organochloride herbicide as well as a plant growth regulator used to control specific annual and perennial grasses. The major food crop use of DPA is on sugarcane and sugar beets. It is also used on various fruits, potatoes, carrots, asparagus, alfalfa, and flax, as well as in forestry, home gardening, and in or near water to control reed and sedge growth.

The following art describes some of the currently known activities and uses of DPA as a herbicide and water disinfectant: *Appl Environ Microbiol.* 2003; 69(8):4375-82; *Environ Microbiol.* 2003; 5(1):48-54; *Chem Res Toxicol.* 1998 11(11): 1332-8; *Bull Environ Contam Toxicol.* 1990; 45(3):343-9; *Radiat Res.* 1973; 54(3):388-97; *J Agric Food Chem.* 1971; 19(1):189-91; *Can J Microbiol.* 1964; 10:843-52; *Appl Microbiol.* 1962; 10:206-10; *Plant Physiol.* 1961; 36(5):698-709; *Plant Physiol.* 1961; 36(5):688-97; *Can J Microbiol.* 1959; 5(3):255-60; and *Science.* 1954; 120(3113):346-347.

DPA is commercially available as its sodium salt or mixed sodium and magnesium salts. In its pure acid form, DPA is a colorless liquid with an acrid odor. As sodium-magnesium salts, it is a white to off-white powder.

DPA has a molecular weight of 142.97 grams/mol; a boiling point of 185-190° C.; a melting point of 20° C.; a relative density of 1.40 (water=1), a solubility in water of 90 g/100 ml at 25° C. and octanol/water partition coefficient of 0.76.

The half-life of DPA in human blood is 1.5-3 days. DPA and all of its known breakdown products dissolve easily in water. They are readily washed from cells and tissues. Because DPA is insoluble in organic solvents and lipids, it does not build up in animal tissues. A non-metabolized form of DPA was excreted in the urine of animals fed the herbicide. Less than 1% of the ingested dose appeared as residues in the milk of dairy cows that were fed DPA. The safety profile of DPA is very good with no observed teratogenic, mitogenic or any other significant systemic adverse effects reported.

Epple and Kirschnick, *Leibigs Annalen,* 1997, issue 1, pages 81-85, teach oligomerization and polymerization in sodium salts of chlorocarboxylic acids such as sodium 2-chloropropionate, sodium 3-chloropropionate and sodium 2-chlorobutyrate.

SUMMARY OF THE INVENTION

The present inventors have surprisingly uncovered that halogenated aliphatic acids, such as dichloropropionic acid (DPA), including salts, complexes and oligomers thereof, are therapeutically potent agents in the treatment of medical conditions associated with neoplastic tissues such as skin and mucosal lesions and tumors. Such halogenated aliphatic acids can further be used intracorporeally, for the treatment of internal neoplasms such as solid malignant tumors.

The present inventors have further uncovered that an oligomer of DPA, a tetramer in particular, is highly efficient in devitalization of all types of neoplastic cells, including malignant cells, a feature that allows performing, subsequent to, prior to or concomitant with the DPA treatment, a surgical procedure to remove the neoplastic tissue, while reducing and even abolishing dissemination of the malignant cells into blood and lymph vessels and thus avoiding distant metastases which may be fatal.

The present inventors have further uncovered that DPA, including salts and oligomers thereof, is capable of inducing systemic immunity and hence can be efficiently utilized in, for example, reducing or preventing appearance or re-appearance of malignant cells, in cases where these are likely to occur.

The present inventors have further designed and successfully prepared and practiced novel oligomers and polymers of DPA, including dimers, tetramers and longer oligomers.

According to an aspect of embodiments of the invention there is provided a method of treating a medical condition associated with neoplastic tissue in a subject in need thereof, the method comprising administering to the subject a devitalizing effective amount of a compound having the general Formula I:

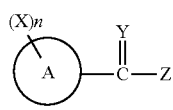

Formula I a pharmaceutical acceptable salt or complex thereof, or an oligomer thereof;
wherein:
Y is O or S;
Z is hydroxy or thiol;
A is a branched or non-branched, substituted on non-substituted, saturated or unsaturated aliphatic hydrocarbon chain having 1-20 carbon atoms in its backbone chain;
X is a halogen substituent of the aliphatic hydrocarbon chain; and
n is an integer from 1 to 10, representing the number of halogen substituents.

According to some embodiments of the invention, the method further comprises surgically removing at least a portion of the neoplastic tissue.

According to an aspect of embodiments of the invention there is provided a use of a compound as described herein in the manufacture of a medicament for treating a medical condition associated with neoplastic tissue.

According to an aspect of embodiments of the invention there is provided a compound as described herein, for use in the treatment of a medical condition associated with neoplastic tissue.

According to some embodiments of the invention Y is O.

According to some embodiments of the invention Z is hydroxy.

According to some embodiments of the invention n is an integer from 1 to 4.

According to some embodiments of the invention, A is selected from the group consisting of methyl, ethyl, propyl, butyl, pentyl, hexyl, heptyl, octyl, nonyl, decyl, undecyl, dodecyl, tridecyl, tetradecyl, pentadecyl, heptadecyl, octadecyl and nonadecyl.

According to some embodiments of the invention, A is selected from the group consisting of methyl, ethyl and propyl.

According to some embodiments of the invention, the compound is selected from the group consisting of ethanoic acid, propanoic acid, butanoic acid, pentanoic acid, hexanoic acid, heptanoic acid, octanoic acid, nonanoic acid, decanoic acid undecanoic acid, dodecanoic acid tridecanoic acid, tetradecanoic acid, pentadecanoic acid, hexadecanoic acid heptadecanoic acid and octadecanoic acid, each being independently substituted by at least one halogen atom.

According to some embodiments of the invention, the compound is selected from the group consisting of ethanoic acid, propanoic acid and butanoic acid, each being independently substituted by at least one halogen atom.

According to some embodiments of the invention, the compound comprises two halogen substituents.

According to some embodiments of the invention, each of the halogen atoms is independently selected from the group consisting of chloro and fluoro.

According to some embodiments of the invention, each of the halogen atoms is chloro.

According to some embodiments of the invention, X is a substituent of a carbon atom positioned from 0 to 2 carbon atoms away from the C(=Y)Z moiety in the hydrocarbon chain.

According to some embodiments of the invention, X is a substituent of a carbon atom adjacent to the C(=Y)Z moiety in the hydrocarbon chain.

According to some embodiments of the invention, A is ethyl.

According to some embodiments of the invention, X is chloro and n is 2.

According to some embodiments of the invention, the compound is 2,2-dichloropropanoic acid.

According to some embodiments of the invention, the compound is in a form of an oligomer thereof.

According to some embodiments of the invention, the oligomer is selected from the group consisting of a trimer, a tetramer, a pentamer, a hexamer, a heptamer, an octamer, a nonamer and a decamer.

According to some embodiments of the invention, the oligomer is selected such that its size selectively fits an intercellular space in the neoplastic tissue and does not fit a normal tissue in close proximity to the neoplastic tissue.

According to some embodiments of the invention, the oligomer is a tetramer.

According to some embodiments of the invention, the oligomer is selected from the group consisting of:

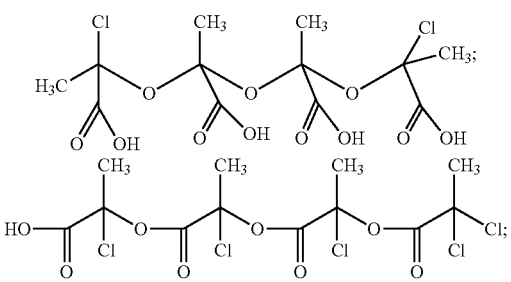

-continued

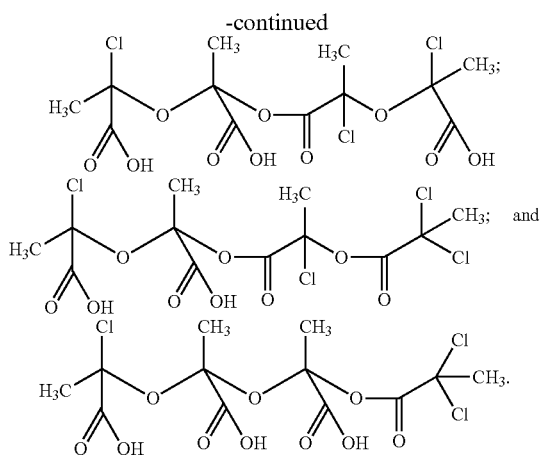

According to some embodiments of the invention, the compound is in a form of a pharmaceutically acceptable salt or a complex of the salt.

According to some embodiments of the invention, the pharmaceutically acceptable salt or complex thereof is selected from the group consisting of a selenium salt, a magnesium salt, a potassium salt, a calcium salt, a zinc salt, a copper salt and an iron salt.

According to some embodiments of the invention, the compound forms a part of a pharmaceutical composition which further comprises a pharmaceutically acceptable carrier.

According to some embodiments of the invention, a concentration of the compound in the composition ranges from 20 weight percents to 100 weight percents of the total weight of the composition. According to some embodiments of the invention, a concentration of the compound in the composition ranges from 70 weight percents to 90 weight percents of the total weight of the composition.

According to some embodiments of the invention, a devitalizing effective amount of the compound ranges from 0.001 ml to 5 ml of the composition per a neoplastic tissue diameter of 1 cm.

According to some embodiments of the invention the neoplastic tissue is selected from the group consisting of viral, benign, premalignant and malignant tissue.

According to some embodiments of the invention the method further comprises surgically removing at least a portion of the neoplastic tissue.

According to some embodiments of the invention, the method is further comprising, subsequent to administering the compound, histologically evaluating the neoplastic tissue.

According to some embodiments of the invention, the medicament is for use in combination with surgically removing at least a portion of the neoplastic tissue.

According to some embodiments of the invention, the medicament is administered prior to, concomitant with, or subsequent to surgically removing the neoplastic tissue.

According to some embodiments of the invention, the medicament is such that subsequent to administering the compound, histologically evaluating the neoplastic tissue can be performed.

According to some embodiments of the invention, the compound is being for use in combination with surgically removing at least a portion of the neoplastic tissue.

According to some embodiments of the invention the compound is being administered prior to, concomitant with, or subsequent to surgically removing the neoplastic tissue.

According to some embodiments of the invention, the compound is being such that subsequent to administering the compound, histologically evaluating the neoplastic tissue can be performed.

According to some embodiments of the invention, the medical condition is associated with malignant neoplastic tissue, the method being for reducing or abolishing dissemination of malignant cells into blood or lymph vessels.

According to some embodiments of the invention, the medical condition is associated with malignant neoplastic tissue, and the medicament is being for reducing or abolishing dissemination of malignant cells into blood or lymph vessels.

According to some embodiments of the invention, the medical condition is associated with malignant neoplastic tissue, and the compound is being for reducing or abolishing dissemination of malignant cells into blood or lymph vessels.

According to some embodiments of the invention, the dissemination of the malignant cells is associated with a surgical procedure.

According to some embodiments of the invention, the neoplastic tissue is a skin or mucosal tissue.

According to some embodiments of the invention, the medical condition is selected from the group consisting of Seborrheic keratosis, Epidermal Nevus, Linear epidermal nevus (unius lateralis), Nevus sebaceus of Jadassohn, Intradermal Nevus, Nevus pilosus, Skin tags and acrochordons, Epidermal inclusion cysts, Sebaceous hyperplasia, Multiple syringomas, Clear cell acanthoma, Compound nevus, Halo Nevi, Spindle cell (Spitz) nevus (epitheloid), Giant Hairy Nevus, Blue Nevus, Nevus of Ota, Dermatofibroma, Angiofibroma, Multiple cherry hemangioma, Pyogenic granuloma, Angiokeratoma, Lymphangioma, Junctional Nevus, Nevus Araneus (Spider telangiectasia), Reclingausen disease, Neurofibromatisis, Steroide form Hyperkeratosis and Papillomatosis, Nevus vasculosus, Nevus depigmentasus, Nevus flammeus (Port-wine stain), Xanthelasma, Verruca vulgaris, Verruca plana, Condiloma acuminatum, Molluscum contagiosum, Actinic keratosis, Cutaneus horn, Bowens disease, Lentigo simplex and senilis, Lentigo maligna, Keratoacanthoma, Trychoepitheliomas, Multiple displastic Nevi, Arsenal keratosis, Juvinel pseudomelanoma, Superficial basal cell carcinoma, Basal cell carcinoma, Nodular basal cell carcinoma, Basal cell pigmented nevus syndrome-Basaliomas, Squamous cell carcinoma, Merkel-trabecular cell carcinoma, Nevus sebaceus of Jadassohn with basal cell carcinoma, Superficial spreading melanoma in situ and stage 1a, Nodullar malignant melanoma in situ and stage 1a, Kaposis hemorrhagic sarcoma (Early macular lesion, non-AIDS related), oral visible lesions, Lentigo malignant melanoma, Papillomas, Fibroepitheliomas, Hemangiomas and Hyperplastic or Hypertrophic Lesions, Neurofibromatosis-1 (Recklinghausen disease), Neurofibromatosis-2, Erosionen (ectopie), Polipus, Posthysterectomie, granuloma, Endocervicitis, cervical viral warts such as molluscus contagious and condiloma acuminate; nabothian cysts; Epistaxis (contact bleeding from erosion of cervix).

According to some embodiments of the invention the medical condition is characterized by multiple skin and/or mucosal lesions.

According to some embodiments of the invention the medical condition is peripheral Neurofibromatosis (Recklinghausen disease).

According to some embodiments of the invention the medical condition is caused by irradiation (e.g., sun irradiation and/or photoirradiation).

According to some embodiments of the invention the administering is effected topically.

According to some embodiments of the invention the medicament is formulated for topical administration.

According to some embodiments of the invention the neoplastic tissue is an internal tissue.

According to some embodiments of the invention the medical condition is selected from the group consisting of acoustic neuroma, adenocarcinoma, angiosarcoma, astrocytoma, bile duct carcinoma, bladder carcinoma, thyroid cancer, tracheal cancer, bone originated tumor such as bone sarcoma, brain tumor such as glioma and neuroblastoma; breast cancer, cervical cancer, chondrosarcoma, chordoma, choriocarcinoma, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, hemangioblastoma, hepatic carcinoma, leiomyosarcoma, liposarcoma, lung carcinoma such as bronchogenic carcinoma, small cell lung carcinoma; lymphangioendotheliosarcoma, lymphangiosarcoma, medullary carcinoma, medulloblastoma, mesothelioma, myxosarcoma, pancreatic cancer, oligodendroglioma, osteogenic sarcoma, ovarian cancer, pancreatic carcinoma, papillary carcinoma, papillary adenocarcinoma, pinealoma, prostate cancer, rectal cancer, kidney cancer such as renal cell carcinoma and Wilms' tumor; retinoblastoma, rhabdomyosarcoma, sebaceous gland carcinoma, seminoma, stomach carcinoma, synovioma, sweat gland carcinoma, testicular tumor, uterus carcinoma, and metastatic disease of the respective primary cancer.

According to some embodiments of the invention the administering of the compound is effected by contacting the neoplastic tissue with the compound.

According to some embodiments of the invention the administering is effected incorporeally.

According to some embodiments of the invention the administering is effected locally, stereotactically or intravascularly.

According to some embodiments of the invention the medicament is formulated for intracorporeal administration.

According to some embodiments of the invention the administration is effected locally, stereotactically or intravascularly.

According to an aspect of embodiments of the invention there is provided a method of reducing or abolishing dissemination of malignant cells into a blood and/or lymph vessel of a subject having a medical condition associated with malignant neoplastic tissue and subjected to a surgical procedure for removing at least a portion of the malignant neoplastic tissue, the method comprising administering to the subject, prior to or concomitant with the surgical procedure, a devitalizing effective amount of a compound as described herein.

According to an aspect of embodiments of the invention there is provided a use of a compound as described herein in the manufacture of a medicament for reducing or abolishing dissemination of malignant cells into a blood and/or lymph vessel of a subject having a medical condition associated with malignant neoplastic tissue and subjected to a surgical procedure for removing at least a portion of the malignant neoplastic tissue.

According to an aspect of embodiments of the invention there is provided a compound as described herein, identified for reducing or abolishing dissemination of malignant cells into a blood and/or lymph vessel of a subject having a medical condition associated with malignant neoplastic tissue and subjected to a surgical procedure for removing at least a portion of the malignant neoplastic tissue.

According to some embodiments of the invention a devitalizing effective amount of the compound ranges from 0.001 ml to 5 ml of the composition per an neoplastic tissue diameter of 1 cm.

According to some embodiments of the invention the neoplastic tissue is skin or mucosal tissue.

According to some embodiments of the invention the medical condition is a metastasizing malignant skin or mucosal tumor.

According to some embodiments of the invention the medical condition is selected from the group consisting of Superficial basal cell carcinoma, Basal cell carcinoma, Nodular basal cell carcinoma, Basal cell pigmented nevus syndrome-Basaliomas, Squamous cell carcinoma, Merkel-trabecular cell carcinoma, Nevus sebaceus of Jadassohn with basal cell carcinoma, Superficial spreading melanoma in situ and stage 1a, Nodullar malignant melanoma in situ and stage 1a, Kaposis hemorrhagic sarcoma (Early macular lesion, non-AIDS related) and Lentigo malignant melanoma.

According to some embodiments of the invention the medical condition is characterized by multiple skin and/or mucosal lesions.

According to some embodiments of the invention the medical condition is caused by irradiation (e.g., sun irradiation and/or photoirradiation).

According to some embodiments of the invention the administering is effected topically.

According to some embodiments of the invention the medicament is formulated for topical administration.

According to some embodiments of the invention the neoplastic tissue is an internal tissue.

According to some embodiments of the invention the administering of the compound is effected by contacting the neoplastic tissue with the compound.

According to some embodiments of the invention the administering is effected intracorporeally.

According to some embodiments of the invention the administering is effected locally, stereotactically and/or intravascularly.

According to some embodiments of the invention the administering is performed during a surgical procedure.

According to some embodiments of the invention the medicament is formulated for intracorporeal administration.

According to some embodiments of the invention the medical condition is selected from the group consisting of acoustic neuroma, adenocarcinoma, angiosarcoma, astrocytoma, bile duct carcinoma, bladder carcinoma, thyroid cancer, tracheal cancer, bone originated tumor such as bone sarcoma, brain tumor such as glioma and neuroblastoma; breast cancer, cervical cancer, chondrosarcoma, chordoma, choriocarcinoma, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, hemangioblastoma, hepatic carcinoma, leiomyosarcoma, liposarcoma, lung carcinoma such as bronchogenic carcinoma, small cell lung carcinoma; lymphangioendotheliosarcoma, lymphangiosarcoma, medullary carcinoma, medulloblastoma, mesothelioma, myxosarcoma, pancreatic cancer, oligodendroglioma, osteogenic sarcoma, ovarian cancer, pancreatic carcinoma, papillary carcinoma, papillary adenocarcinoma, pinealoma, prostate cancer, rectal cancer, kidney cancer such as renal cell carcinoma and Wilms' tumor; retinoblastoma, rhabdomyosarcoma, sebaceous gland carcinoma, seminoma, stomach carcinoma, synovioma, sweat gland carcinoma, testicular tumor, uterus carcinoma, or metastatic disease of the respective primary cancer.

According to an aspect of embodiments of the invention there is provided a method of inducing a systemic immune response to pre-malignant, and/or potentially malignant cells, the method comprising administering to a subject in need thereof a therapeutically effective amount of a compound as described herein.

According to an aspect of embodiments of the invention there is provided a use of a compound as described herein in the manufacture of a medicament for inducing a systemic immune response to pre-malignant, and/or potentially malignant cells.

According to an aspect of embodiments of the invention there is provided a compound as described herein for reducing or abolishing dissemination of malignant cells into a blood and/or lymph vessel of a subject having a medical condition associated with malignant neoplastic tissue and subjected to a surgical procedure for removing at least a portion of the malignant neoplastic tissue.

According to an aspect of embodiments of the invention there is provided a method of inducing a systemic immune response to malignant cells, the method comprising administering to a subject in need thereof a therapeutically effective amount of a compound as described herein.

According to an aspect of embodiments of the invention there is provided a use of a compound as described herein in the manufacture of a medicament for inducing a systemic immune response to malignant cells.

According to an aspect of embodiments of the invention there is provided a compound as described herein for inducing a systemic immune response to malignant cells.

According to some embodiments of the invention, the administering is effected topically.

According to some embodiments of the invention, the administering is effected intracorporeally.

According to some embodiments of the invention, the medicament is formulated for topical administration.

According to some embodiments of the invention, the medicament is formulated for intracorporeal administration.

According to some embodiments of the invention, the systemic immune response is an innate immune response or an acquired immune response.

According to some embodiments of the invention, the method is further comprising administering to the subject at least one immunostimulating agent.

According to some embodiments of the invention, the medicament further comprises at least one immunostimulating agent.

According to some embodiments of the invention, the compound is for use in combination with at least one immunostimulating agent.

According to some embodiments of the invention, the immunostimulating agent is Granulocyte-macrophage colony-stimulating factor.

According to an aspect of embodiments of the invention there is provided a use of a compound as described herein in the manufacture of a medicament.

According to an aspect of embodiments of the invention there is provided a pharmaceutical composition comprising, as an active ingredient, the compound as described herein, and a pharmaceutically acceptable carrier.

According to some embodiments of the invention, the composition is being packaged in a packaging material and identified in print, in or on the packaging material, for use in the treatment of a medical condition associated with a neoplastic tissue.

According to some embodiments of the invention, the composition is being packaged in a packaging material and identified in print, in or on the packaging material, for use in reducing or preventing dissemination of malignant cells into a blood and/or lymph vessel of a subject having a medical condition associated with malignant neoplastic tissue and subjected to a surgical procedure for removing at least a portion of the malignant neoplastic tissue.

According to an aspect of embodiments of the invention there is provided an oligomer of a compound having a general Formula I, as described herein.

According to some embodiments of the invention, the oligomer is being selected from the group consisting of a trimer, a tetramer, a pentamer, a hexamer, a heptamer, an octamer, a nonamer and a decamer.

According to some embodiments of the invention, the oligomer is being a tetramer.

According to some embodiments of the invention, the oligomer is selected from the group consisting of:

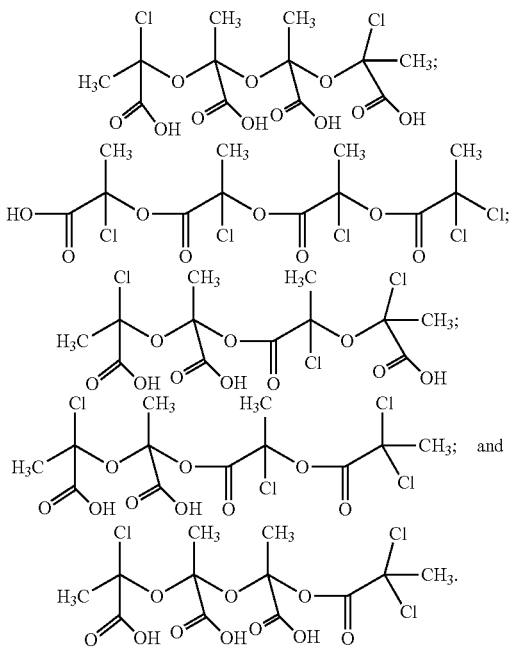

According to an aspect of embodiments of the invention there is provided a pharmaceutical composition comprising, as an active ingredient, the oligomer as described herein and a pharmaceutically acceptable carrier.

According to some embodiments of the invention, the composition further comprises at least one selenium-containing compound.

According to some embodiments of the invention, the selenium-containing compound is selected from the group consisting of a selenium salt, a selenium oxide, a selenium halide, a selenium acid or a combination thereof.

According to an aspect of embodiments of the invention there is provided a process of preparing the oligomer as described herein, the process comprising heating a compound as described herein, in a monomer form thereof, in the presence of an aqueous solution, at a temperature ranging between 150° C. and 250° C., thereby obtaining the oligomer.

According to some embodiments of the invention, an amount of the aqueous solution ranges from 0 to 50 weight percents.

According to some embodiments of the invention, the heating is at a temperature of 190° C.

According to some embodiments of the invention, the heating is for a time period that ranges from 0 to 12 hours.

According to some embodiments of the invention, the heating is for a time period of at least two hours.

According to some embodiments of the invention, the heating is for a time period of at least four hours.

According to some embodiments of the invention, the heating is for a time period of at least six hours.

According to some embodiments of the invention, the process further comprises admixing with the oligomer an additional agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
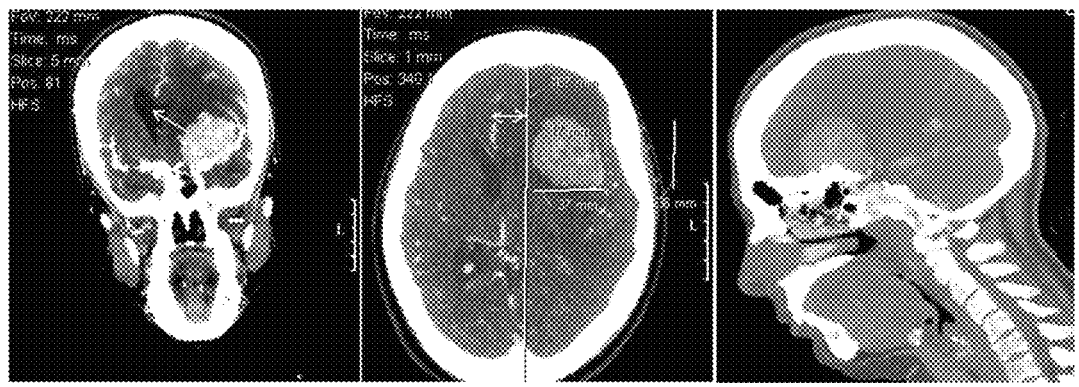
Figure 1B:
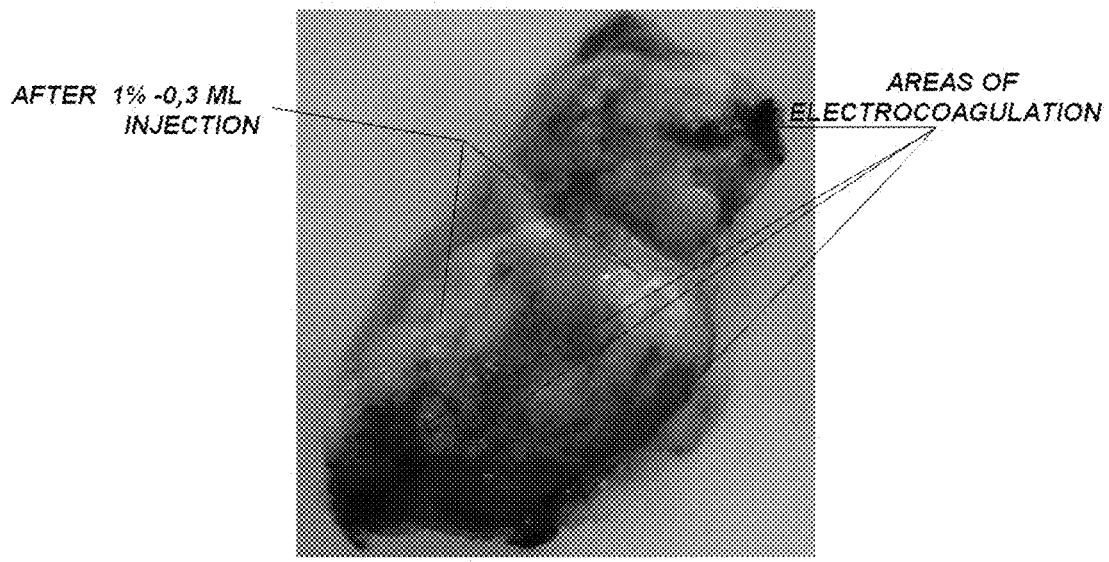
Figure 1C:
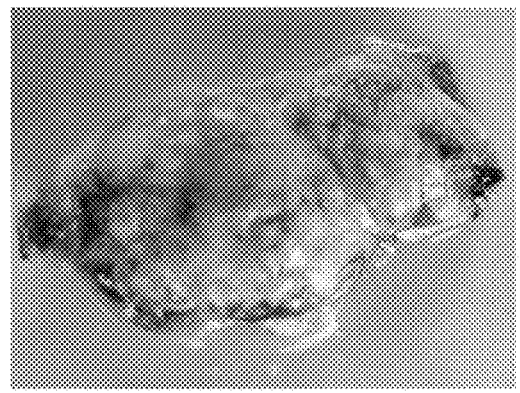
Figure 1D:
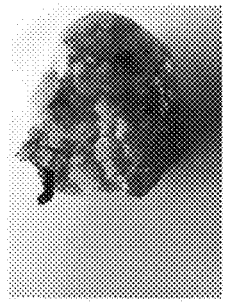
Figure 1D:
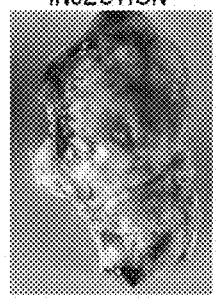

FIGS. 1A-D present photographs showing data obtained during treating of meningioma with a DPA oligomer according to exemplary embodiments of the invention. FIG. 1A present images obtained by CTA 3D-MPR, showing the presence of a base skull meningioma. FIG. 1B is an image of the tumor a day after its removal by LT Pterional craniotomy, and 1 minute after injecting to the tumor a solution containing 0.3% by weight a DPA oligomer according to exemplary embodiments of the invention. FIG. 1C is an image of the tumor 3 minutes after injecting thereto a solution containing a DPA oligomer. FIG. 1D presents the devitalization process that occurred in the excised meningioma following treatment with a solution containing a DPA oligomer according to exemplary embodiments of the invention.

DESCRIPTION OF SPECIFIC EMBODIMENTS OF THE INVENTION

The present invention, in some embodiments thereof, relates to compounds, compositions, uses thereof and methods utilizing same for treating disorders associated with neoplastic tissues, such as, for example, skin and mucosal tumors and lesions, as well as internal tumors.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Neoplasia is defined as the abnormal proliferation of cells, and mostly results in a lump or a tumor. Disorders associated with neoplastic tissue include, for example, viral infections and cancer. Current methods of treating neoplasia include surgery, chemotherapy and radiation. None of these methods are optimal and each suffer from drawbacks such as life threatening adverse effects and complications, pain, high cost as well as, in the case of chemotherapy and radiation, development of resistance to therapy.

One of the main concerns when using a surgical procedure for treating cancer such as skin and mucosal related cancer is the intraoperative dissemination of malignant cells into blood or lymph vessels. Shedding of malignant cells into the circulation of a patient during surgery is one of the mechanisms of postoperative tumor metastasis and is associated with a very poor prognosis.

The present inventors have surprisingly uncovered that halogenated aliphatic acids, such as dichloropropionic acid (DPA), including salts, oligomers and complexes thereof, are therapeutically potent agents in the treatment of medical conditions associated with neoplastic tissue such as skin and mucosal lesions and tumors.

2,2-Dichloropropanoic acid ($CH_3$—$CCl_2$—$C(=O)OH$; DPA; Dalaphon; CAS No. 75-99-0) is a chemical widely used as a water disinfectant and is also used as an organochloride herbicide and as a plant growth regulator used to control specific annual and perennial grasses. DPA is commercially available as its sodium salt or mixed sodium and magnesium salts.

The half-life of DPA in human blood is 1.5-3 days. DPA and all of its known breakdown products dissolve easily in water. They are readily washed from cells and tissues. Because DPA is insoluble in organic solvents and lipids, it does not build up in animal tissues. The safety profile of DPA is very good, with no observed teratogenic, mitogenic or any other significant systemic adverse effects reported.

The use of DPA in the treatment of medical disorders has never been reported hitherto.

As detailed in the Examples section that follows, the present inventors have now surprisingly uncovered that the halogenated aliphatic acid DPA and oligomers thereof are therapeutically potent agents for treating neoplasia conditions of the skin and mucosal tissue. Specifically, in clinical studies which included 6938 patients suffering from various skin pathologies, topical administration of DPA and DPA oligomers onto benign, viral, pre-malignant, non-metastasizing malignant and mucosal neoplasms, resulted in effective treatment of these neoplasms with very good clinical results observed in 82.1% of the neoplasms and a satisfactory level of clinical results observed in 99.1% of the neoplasms (see, Table 10). The level of neoplasm recurrence following DPA and DPA oligomer treatment during the 2-8 year follow-up period was only 2.3%, 6.1%, 3.5%, 2.8% and 1.2% for benign, viral, pre-malignant, non-metastasizing malignant and mucosal tumors, respectively (see, Table 11). Furthermore, no occurrences of regional and distant metastases of the skin tumors as well as lethality cases were observed. The results further show that the high efficacy of DPA and DPA oligomer treatment was observed in all treated skin tumor or lesion and was not dependent on the type of tumor/lesion, age, skin color or gender of the patient. With regard to the safety of DPA, no systemic toxicity was detected in any of the treated patients and only a short term local allergic reaction, pain and itching were observed in 5.8% of the patients during the treatment period, with a possible development of visible skin hypo- or hyperpigmentation, as well as scar and kelloid formation.

Additional studies have also shown a similar therapeutic pattern (see, Example 2 in the Examples section that follows). Upon treatment with DPA or DPA oligomer, and a 2-year follow-up period, less then 2% neoplasm recurrence was observed for benign and pre-malignant neoplasms, and no neoplasm recurrence was observed for malignant neoplasms.

In vivo animal studies have shown that treatment with DPA or a DPA oligomer do not adversely affect the immunological response of the treated animals (see, Example 3).

Additional in vivo studies have shown that treatment of mice having breast cancer with DPA oligomer during a surgical removal of the tumor resulted in reduced metastases and enhanced survivability of the treated animals as compared to untreated control (see, Example 5).

Studies conducted on meningioma have shown that treating a surgically removed tumor with a DPA oligomer resulted in devitalization of the tumor (see, Example 6, and FIGS. 1A-D).

Thus, it has been observed that the practiced halogenated aliphatic acid, DPA and oligomeric forms thereof, are practically non-toxic, exhibit a strongly localized action, are not absorbed into the organism and have no systemic, teratogenic, embryotoxic or carcinogenic properties. These compounds exhibit neither significant side effects nor contraindication for use.

These results further demonstrate the beneficial and high therapeutic efficacy of halogenated aliphatic carboxylic acids such as DPA, and of oligomers thereof, in the treatment of medical conditions associated with neoplastic tissue, including, for example, viral, benign, premalignant and malignant tumors.

Thus, in accordance with an aspect of some embodiments the present invention, there is provided a method of treating a medical condition associated with neoplastic tissue in a subject in need thereof. The method, according to these embodiments, is effected by administering to the subject a devitalizing effective amount of a compound, as described herein.

The phrase "neoplastic tissue", as used herein, describes a tissue, as defined herein, that is formed by uncontrolled, progressive proliferation of cells, and which is no longer under normal bodily control and serving no physiological function. The growth of a neoplastic tissue typically exceeds, and is uncoordinated with, that of the normal tissues around it and usually causes a lump or tumor. The phrase "neoplastic tissue" is also referred to herein and in the art as "tumor" and encompasses benign, viral, pro-malignant and malignant tumors.

The term "tissue" describes an ensemble of cells, not necessarily identical, but from the same origin, that together carry out a specific function.

Tissue cells proliferate up to normal limits with various physiological signal molecules such as apoptotic factors and growth factors regulating their proliferation (for example toxins, hormones, growth factors, nitric oxide, or cytokines). In the case of neoplastic tissue, the growth of a clone of cells is less controlled than, and is uncoordinated with, that of the normal tissues surrounding it.

The term "devitalizing" describes the ability of a substance to incapacitate a cell such that it is no longer functional (or vital), while not necessarily affecting its structure and content (as opposed to apoptosis, lysis, etc.). A "devitalized" cell is unable to function in the same manner it did before devitalization and hence, for example, can no longer grow or divide. For example, a metastatic cancer cell could be devitalized not only by killing the cell via lysis, necrosis, or programmed cell death (apoptosis), but could be made to be no longer able to divide. In another example, devitalizing a cell can be affected via dehydration or freezing.

The term "a devitalizing effective amount" describes an amount of a compound as described herein effective to devitalize a neoplastic tissue to an extent which significantly reduces the size and/or growth of, or completely abolishes, the neoplastic tissue of the subject being treated.

Accordingly, in the case of a medical condition associated with the neoplastic tissue, the term "a devitalizing effective amount" describes an amount of a compound as described herein effective to devitalize a neoplastic tissue to an extent which prevents, alleviates or ameliorates symptoms of the medical condition and/or prolongs the survival of the subject being treated.

Determination of a devitalizing effective amount is well within the capability of those skilled in the art, especially in light of the detailed disclosure provided herein.

The term "subject" (alternatively referred to herein as "patient"), as used herein, refers to an animal, preferably a mammal, most preferably a human, who has been the object of treatment, observation or experiment.

Accordingly, in accordance with another aspect of some embodiments of the present invention there is provided a use of a compound as described herein in the manufacture of a medicament for treating a medical condition associated with neoplastic tissue.

The compounds, according to embodiments of the present invention, can be collectively represented by the general formula I as follows:

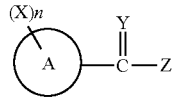

Formula I a pharmaceutical acceptable salt or complex thereof or an oligomer form thereof;
wherein:
Y is O or S;
Z is hydroxy or thiol;
A is a branched or non-branched, substituted on non-substituted, saturated or unsaturated aliphatic hydrocarbon chain having 1-20 carbon atoms in its backbone chain;
X is a halogen substituent of said aliphatic hydrocarbon chain; and
n is an integer from 1 to 10, representing the number of halogen substituents.

In some embodiments Y is O, such that the compounds described herein are halogenated aliphatic carboxylic acids.

In some embodiments Z is hydroxy.

In other embodiments, the compounds described herein are halogenated aliphatic thiocarboxylic acids, such that Y is S and/or Z is thiol.

In some embodiments, n is an integer from 1 to 4.

Compounds in which n is 1 are referred to as monohalogenated; compounds in which n is 2 are referred to as dihalogenated and compounds on which n is greater than 2 are referred to as polyhalogenated.

The term "hydroxy" describes an —OH group.
The term "thiol" describes an —SH group.

The phrase "aliphatic hydrocarbon chain" describes an organic moiety composed mainly of carbon and hydrogen atoms, in which the carbon atoms are linked to one another and forming an aliphatic (non-cyclic) backbone chain. The aliphatic hydrocarbon chain can be saturated or unsaturated, linear or branched, and can be interrupted by one or more heteroatoms such as oxygen, sulfur and/or nitrogen (e.g., —NH—).

In some embodiments, the term "aliphatic hydrocarbon chain" encompasses any one or a combination of alkyl, alkenyl, and alkynyl.

The term "alkyl" describes a saturated aliphatic hydrocarbon including straight chain and branched chain groups. Preferably, the alkyl group has 1 to 30 carbon atoms. Whenever a numerical range; e.g., "1-30", is stated herein, it means that the group, in this case the alkyl group, may contain 1 carbon atom, 2 carbon atoms, 3 carbon atoms, etc., up to and including 30 carbon atoms. In some embodiments the alkyl group has 1-20 carbon atoms. In some embodiments, the alkyl group has 1-10 carbon atoms. In some embodiments, the alkyl group has 1-4 carbon atoms. Exemplary alkyl groups include, but are not limited to methyl, ethyl, propyl, butyl, pentyl, hexyl, heptyl, octyl, nonyl, decyl, undecyl, dodecyl, tridecyl, tetradecyl, pentadecyl, heptadecyl, octadecyl and nonadecyl.

The term "alkenyl" describes an alkyl group, as defined herein, which consists of at least two carbon atoms and at least one carbon-carbon double bond.

The term "alkynyl" describes an alkyl group, as defined herein, which consists of at least two carbon atoms and at least one carbon-carbon triple bond.

The aliphatic hydrocarbon chain may be unsubstituted or substituted by one or more substituents other then hydrogen or the halogen represented by X in the general formula hereinabove. When substituted, the substituent group can be, for example, alkyl, cycloalkyl, aryl, heteroaryl, heteroalicyclic, hydroxy, alkoxy, aryloxy, thiohydroxy, thioalkoxy, thioaryloxy, cyano, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethanesulfonamido, silyl, guanyl, guanidino, ureido, amino or NRaRb, as defined herein, wherein Ra and Rb are each independently hydrogen, alkyl, cycloalkyl, aryl, carbonyl, sulfonyl, trihalomethysulfonyl and, when combined, a five- or six-member heteroalicyclic ring.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, hydroxy, alkoxy, aryloxy, thiohydroxy, thioalkoxy, thioaryloxy, cyano, halo, carbonyl, thiocarbonyl, C-carboxy, O-carboxy, O-carbamyl, N-carbamyl, C-amido, N-amido, nitro, amino and NRaRb as defined hereinabove.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, trihalomethyl, alkyl, hydroxy, alkoxy, aryloxy, thiohydroxy, thiocarbonyl, C-carboxy, O-carboxy, O-carbamyl, N-carbamyl, O-thiocarbamyl, N-thiocarbamyl, C-amido, N-amido, sulfinyl, sulfonyl, amino and NRaRb as defined hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, halo, trihalomethyl, hydroxy, alkoxy, aryloxy, thiohydroxy, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino or NRaRb as defined above.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, alkyl, cycloalkyl, aryl, heteroaryl, halo, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and NRaRb as defined above.

The term "alkoxy" describes both an —O-alkyl and an —O-cycloalkyl group, as defined herein.

The term "aryloxy" describes both an —O-aryl and an —O-heteroaryl group, as defined herein.

The term "thioalkoxy" describes both an —S-alkyl group, and an —S-cycloalkyl group, as defined herein.

The term "thioaryloxy" refers to both an —S-aryl and an —S-heteroaryl group, as defined herein.

The term "cyano" describes a —C≡N group.

The term "carbonyl" describes a —C(═O)—R' group, where R' is hydrogen, alkyl, cycloalkyl, aryl, heteroaryl (bonded through a ring carbon) or heteroalicyclic (bonded through a ring carbon) as defined herein.

The term "thiocarbonyl" describes a —C(═S)—R' group, where R' is as defined herein.

The term "O-carbamyl" describes an —OC(═O)—NR'R" group, where R' is as defined herein and R" is hydrogen, alkyl, cycloalkyl, aryl, heteroaryl (bonded through a ring carbon) or heteroalicyclic (bonded through a ring carbon) as defined herein.

The term "N-carbamyl" describes an R'OC(═O)—NR"— group, where R' and R" are as defined herein.

The term "O-thiocarbamyl" describes an —OC(═S)—NR'R" group, where R' and R" are as defined herein.

The term "N-thiocarbamyl" describes an R"OC(═S) NR'— group, where R' and R" are as defined herein.

The term "C-amido" describes a —C(═O)—NR'R" group, where R' and R" are as defined herein.

The term "N-amido" describes an R'C(═O)—NR" group, where R' and R" are as defined herein.

The term "C-carboxy" describes a —C(═O)—O—R' groups, where R' is as defined herein.

The term "O-carboxy" describes an R'C(═O)—O— group, where R' is as defined herein.

The term "nitro" group describes an —NO₂ group.

The term "sulfonamide", encompasses both an "S-sulfonamido" and "N-sulfonamido" wherein an "S-sulfonamido" group describes a —S(═O)₂—NR'R" group, with R' is as defined herein and R" is as defined for R'. An "N-sulfonamido" group describes an R'S(=O)₂—NR" group, where R' and R" are as defined herein.

The term "trihalomethanesulfonamido" group refers to an T₃CS(=O)₂NR'— group, wherein T is a halo group as defined herein and R' is as defined herein.

The term "guanidino" group describes an —R'NC(=N)—NR"R'" group, where R', R" and R'" is hydrogen, alkyl, cycloalkyl, aryl, heteroaryl (bonded through a ring carbon) or heteroalicyclic (bonded through a ring carbon) as defined herein.

The term "guanyl" group describes an R'R"NC(=N)— group, where R' and R" are as defined herein.

The term "silyl" describes a —SiR'R"R'", where R', R" and R'" are as defined herein.

The term "ureido" group describes an —NR'C(=O)—NR"R'" group, where R', R" and R'" are as defined herein.

The term "amino" group describes an —NH₂ group.

The term "sulfonyl" group describes an —S(=O)₂—R' group, where R' is as defined herein.

The term "halogen" or "halo" describes fluoro, chloro, bromo or iodo atom.

In some embodiments, A is methyl, ethyl, propyl, butyl, pentyl, hexyl, heptyl, octyl, nonyl, decyl, undecyl, dodecyl, tridecyl, tetradecyl, pentadecyl, heptadecyl, octadecyl or nonadecyl. In some embodiments, A is methyl, ethyl or propyl. In some embodiments, A is ethyl.

In some embodiments, the compound is ethanoic acid (acetic acid), propanoic acid, butanoic acid, pentanoic acid, hexanoic acid, heptanoic acid, octanoic acid, nonanoic acid, decanoic acid undecanoic acid, dodecanoic acid tridecanoic acid, tetradecanoic acid, pentadecanoic acid, hexadecanoic acid heptadecanoic acid or octadecanoic acid, each being independently substituted by at least one halogen atom.

In some embodiments, the compound is ethanoic acid, propanoic acid and butanoic acid, each being independently substituted by at least one halogen atom.

In some embodiments, the compound having general formula I comprises two or more halogen substituents (such that n is greater than 1). The halogen substituents can be the same or different. In cases where the hydrocarbon chain comprises more than one carbon atom, the halogen substituents can be on the same carbon atom in the hydrocarbon chain, or on different carbon atoms in the hydrocarbon chain.

In some embodiments, each of the halogen atoms is independently chloro or fluoro.

In some embodiments, the compound comprises two halogen substituents.

Without being bound by any particular theory, it is speculated that the high devitalizing activity of the halogenated aliphatic acids described herein is due to the positioning of the halogen atoms in close proximity to the carboxylic (or thiocarboxylic) moiety, which enhances the acidity of the compound due to the electron withdrawing effect of the halogen substituent.

Accordingly, in some embodiments, X in the general formula described herein is a halogen substituent or substituents of a carbon atom positioned from 0 to 2 carbon atoms away from the C(=Y)Z moiety in the hydrocarbon chain.

In some embodiments, X is a substituent of a carbon atom adjacent to the C(=Y)Z moiety in the hydrocarbon chain. The phrase "adjacent to the C(=Y)Z moiety", as used herein, is to indicate that the X substituent is located 0 carbons away from the C(=Y)Z moiety, namely, at position a to the carboxylic (or thiocarboxylic) moiety.

A carbon atom positioned 1 carbon away from the carboxylic (or thiocarboxylic moiety) is located at position 13 to the carboxylic (or thiocarboxylic) moiety.

In some embodiments, A in the general formula I is ethyl, such that the compound is a halogenated propionic acid (also referred to herein as halogenated propanoic acid).

In some embodiments, X is chloro and n is 2, such that the compound is dihalogenated, namely, dichlorinated.

In some embodiments, the compound is 2,2-dichloropropanoic acid (DPA).

Additional exemplary compounds include, but are not limited to, 2-chloropropanoic acid, 3-chloropropanoic acid, 2,3-dichloropropanoic acid, 3,3-dichloropropanoic acid, 2-chlorobutanoic acid, 2,2-dichlorobutanoic acid, 3-chlorobutanoic acid, 2,3-dichlorobutanoic acid, 3,3-dichlorobutanoic acid, 2,2-dichloropentanoic acid, 2-chloropentanoic acid, 3-chloropentanoic acid, 2,3-dichloropentanoic acid, 3,3-dichloropentanoic acid, 2-chlorohexanoic acid, 2,2-dichlorohexanoic acid, 3-chlorohexanoic acid, 2,3-dichlorohexanoic acid, 3,3-dichlorohexanoic acid, 2-fluoropropanoic acid, 3-fluoropropanoic acid, 2,3-difluoropropanoic acid, 3,3-difluoropropanoic acid, 2-fluorobutanoic acid, 2,2-difluorobutanoic acid, 3-fluorobutanoic acid, 2,3-difluorobutanoic acid, 3,3-difluorobutanoic acid, 2,2-difluoropentanoic acid, 2-fluoropentanoic acid, 3-fluoropentanoic acid, 2,3-difluoropentanoic acid, 3,3-difluoropentanoic acid, 2-fluorohexanoic acid, 2,2-difluorohexanoic acid, 3-fluorohexanoic acid, 2,3-difluorohexanoic acid, 3,3-difluorohexanoic acid, 2,2-fluorochloropropanoic acid, 2,3-fluorochloropropanoic acid, 3,3-fluorchloropropanoic acid, 2,2-fluorochlorobutanoic acid, 2,3-fluorochlorobutanoic acid, 3,3-fluorochlorobutanoic acid, 2,2-fluorochloropentanoic acid, 2,3-fluorochloropentanoic acid, 3,3-fluorochloropentanoic acid, 2,2-fluorochlorohexanoic acid, 2,3-fluorochlorohexanoic acid, 3,3-fluorochlorohexanoic acid, 2,2,3-trichloropropanoic acid, 2,3,3-trichloropropanoic acid, 3,3,3-trichloropropanoic acid, 2,2,3-trifluoropropanoic acid, 2,3,3-trifluoropropanoic acid, 3,3,3-trifluoropropanoic acid, 2-chloro-2,3-difluloropropanoic acid, 2-chloro-3,3-difluoropropanoic acid, 2,2-dichloro-3-fluoropropanoic acid, 2,2-difluoro-3-chloropropanoic acid, 2,2,3-trichlorobutanoic acid, 2,3,3-trichlorobutanoic acid, 3,3,3-trichlorobutanoic acid, 2,2,3-trifluorobutanoic acid, 2,3,3-trifluorobutanoic acid, 3,3,3-trifluorobutanoic acid, 2-chloro-2,3-diflulorobutanoic acid, 2-chloro-3,3-difluorobutanoic acid, 2,2-dichloro-3-fluorobutanoic acid, 2,2-difluoro-3-chlorobutanoic acid, 2,2,3-trichloropentanoic acid, 2,3,3-trichloropentanoic acid, 3,3,3-trichloropentanoic acid, 2,2,3-trifluoropentanoic acid, 2,3,3-trifluoropentanoic acid, 3,3,3-trifluoropentanoic acid, 2-chloro-2,3-difluloropentanoic acid, 2-chloro-3,3-difluoropentanoic acid, 2,2-dichloro-3-fluoropentanoic acid, 2,2-difluoro-3-chloropentanoic acid, 2,2,3-trichlorohexanoic acid, 2,3,3-trichlorohexanoic acid, 3,3,3-trichlorohexanoic acid, 2,2,3-trifluorohexanoic acid, 2,3,3-trifluorohexanoic acid, 3,3,3-trifluorohexanoic acid, 2-chloro-2,3-diflulorohexanoic acid, 2-chloro-3,3-difluorohexanoic acid, 2,2-dichloro-3-fluorohexanoic acid, 2,2-difluoro-3-chlorohexanoic acid, and any additional structural analogs thereof.

The present embodiments further encompass any pharmaceutically acceptable salt, complexes, prodrugs, solvates, hydrates and, if present, purified enantiomers of each of the compounds described herein.

The phrase "pharmaceutically acceptable salt" refers to a charged species of the parent compound and its counter ion. A "pharmaceutically acceptable salt" is typically used to modify the solubility characteristics of the parent compound and/or to reduce any significant irritation to an organism by the parent compound, while not abrogating the biological activity and properties of the administered compound. In the context of the present embodiments, a pharmaceutically acceptable salt can be, for example, an ionized form of the carboxylic or thiocarboxylic moiety, as a carboxylate or thiocarboxylate anion, and a cation.

In some cases, a pharmaceutically acceptable complex of the compound is formed when the parent compound interacts with another species via coordinative interactions (as opposed to the electrostatic interactions involved in salts). Such complexes can be formed, for example, between the carboxylic (or thiocarboxylic) moiety and a species that can coordinatively bind to this moiety. Exemplary complexes can be formed with species such as, but not limited to metallic selenium, zinc, copper, iron, and the like, including salts and oxides thereof. Exemplary complexes are formed with selenium, selenium oxide or selenium salt.

In some embodiments, the pharmaceutically acceptable salt is selected from the group consisting of a sodium salt, a magnesium salt, a potassium salt, and a calcium salt.

As discussed in detail hereinbelow, in some embodiments, pharmaceutically acceptable salts and complexes of the compounds described herein are used for improving the performance of the compounds described herein.

As used herein, the term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo.

The term "solvate" refers to a complex of variable stoichiometry (e.g., di-, tri-, tetra-, penta-, hexa-, and so on), which is formed by a solute (the compound described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

In some embodiments, the compound is in a form of an oligomer thereof, as defined hereinunder.

Oligomeric forms of such compounds in general and of DPA in particular have not been described hitherto and hence, according to another aspect of some embodiments of the present invention there is provided an oligomer of a compound having a general Formula I, as described herein. The present embodiments further encompass any pharmaceutically acceptable salts and complexes, prodrugs, solvates, hydrates and, if present, purified stereomers of each of the oligomers described herein.

The term "oligomer", as used herein, describes a compound that comprises two or more repeating units condensed one with another. An "oligomer", as described herein, is therefore produced by the condensation of two or more monomeric units composing the same. Accordingly, an oligomeric form of a compound as described herein describes a plurality of repeating units of the monomeric form of the compound as described herein. The term "oligomer" is meant to encompass, without limitation, oligomers incorporating up to, e.g., 50 monomeric units, including, but not limited to, oligomers composed of 2 monomeric units (i.e. dimmer), 3 monomeric units (i.e. trimmer), 4 monomeric units (i.e. tetramer), 5 monomeric units (i.e. pentamer), 6 monomeric units (i.e. hexamer), 7 monomeric units (i.e. heptamer), 8 monomeric units (i.e. octamer), 9 monomeric units (i.e. nanomer), 10 monomeric units (i.e. decamer), 11 monomeric units, 12 monomeric units, 13 monomeric units, 14 monomeric units, 15 monomeric units, 16 monomeric units, 17 monomeric units, 18 monomeric units, 19 monomeric units, 20 monomeric units, 21 monomeric units, 22 monomeric units, 23 monomeric units, 24 monomeric units, 25 monomeric units, 26 monomeric units, 27 monomeric units, 28 monomeric units, 29 monomeric units, 30 monomeric units, 31 monomeric units, 32 monomeric units, 33 monomeric units, 34 monomeric units, 35 monomeric units, 36 monomeric units, 37 monomeric units, 38 monomeric units, 39 monomeric units, 40 monomeric units, 41 monomeric units, 42 monomeric units, 43 monomeric units, 44 monomeric units, 45 monomeric units, 46 monomeric units, 47 monomeric units, 48 monomeric units, 49 monomeric units and 50 monomeric units.

In some embodiments, the oligomer is selected from the group consisting of a trimmer, a tetramer, a pentamer, a hexamer, a heptamer, an octamer, a nonamer and a decamer. In some embodiments, the oligomer is a tetramer.

As detailed in the Examples section that follows, novel oligomers of DPA were successfully synthesized and tested.

As discussed hereinabove, the devitalizing activity of a DPA oligomer, an exemplary oligomer according to some embodiments of the invention, is demonstrated in the Examples section that follows. Specifically, the administration of DPA oligomers was therapeutically beneficial in the treatment of viral, benign, premalignant and malignant skin and mucosal tumors/lesions (see, Tables 10 and 11).

Exemplary DPA oligomers include, but are not limited to:

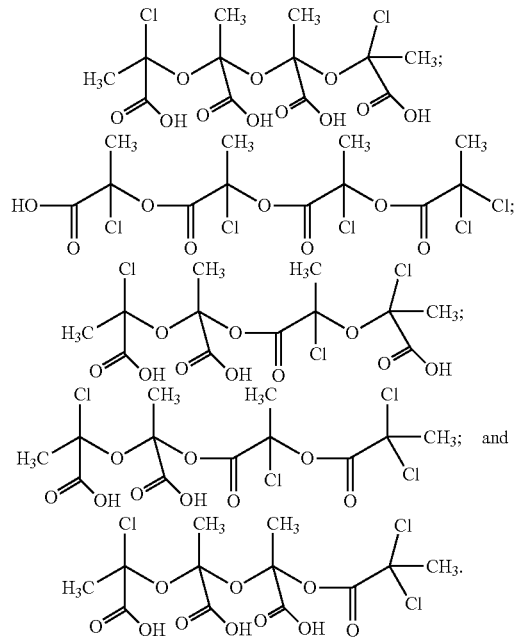

The oligomers described herein may be synthesized via the condensation and formation of ether and ester bonds between the monomeric units.

Further according to embodiments of the present invention, there are provided processes of preparing the novel oligomers described herein. These processes are described in detail in the Examples section that follows.

Thus, according to another aspect of some embodiments of the present invention there is provided a process of preparing the oligomers described herein, the process being effected by heating a compound as described herein, in a monomer form thereof, in the presence of an aqueous solution, at a temperature ranging from 150° C. to 250° C., thereby obtaining the oligomer.

Without being bound to any particular theory, it is speculated that the process described herein includes dehydrolysis, caramelization and/or pyrolysis, and that the occurrence of these reactions depend on the time and temperature at which the process is performed.

In some embodiments, the amount of water in the aqueous solution ranges from 0 to 50 weight percents, or from 0.1 to 50 weight percents.

In some embodiments, the heating is at a temperature that ranges from 170° C. to 220° C., or from 180° C. to 200° C. In some embodiments, the heating is at a temperature of 190° C.

In some embodiments, the heating is for a time period that ranges from 0.5 to 12 hours.

The length of the oligomer is dependent on the heating time period whereby longer oligomers (i.e. comprised of more monomeric units) are synthesized using longer heating time periods. The tetrameric form of DPA is synthesized by the process described herein with a heating time period of about four hours.

In some embodiments, the heating is for a time period of at least two hours.

In some embodiments, the heating is for a time period of at least four hours.

In some embodiments, the heating is for a time period of at least six hours.

The process described herein may further comprise admixing with the oligomer an additional agent. Such an agent may be, for example, selenium or a selenium containing compound (e.g., a selenium oxide, a selenium salt or a selenium complex).

The present inventors have observed that the size of the oligomer affects its devitalizing activity. Without being bound by theory, it is speculated that neoplastic tissues are less dense, having larger intercellular spaces between the neoplastic cells, as compared to normal tissues. This looser structure enables the selective penetration of larger sized oligomers into neoplastic tissue and much less to normal tissue, thereby reducing adverse effects associated with the undesired activity of the compound against normal tissue.

Therefore, in some embodiments, the oligomer is selected such that its size selectively fits an intercellular space in the neoplastic tissue and does not fit a normal tissue in close proximity to the neoplastic tissue.

While further analyzing the results of the clinical studies presented hereinbelow, the inventors have surprisingly uncovered that the administration of the tetrameric form of DPA is more therapeutically beneficial for treating benign skin and mucosal tumors and lesions whereas administration of lengthier oligomers is more therapeutically beneficial for treating premalignant and malignant skin and mucosal tumors. Without being bound by a particular theory, it is suggested that this observed difference in activity is due to the looser packing of premalignant and malignant neoplastic tissue as compared to benign neoplastic tissue whereby lengthier oligomers are less able to penetrate into benign neoplastic tissue yet are able to penetrate into premalignant and malignant neoplastic tissue. In contrast, monomers or tetramers, being smaller in size, are able to penetrate benign neoplastic tissue and thus are more suitable for treating such tumors/lesions.

Hence, in some embodiments of the present invention, the method described herein is for treating a medical condition associated with benign neoplastic tissue in a subject in need thereof, and is effected by administering to the subject a devitalizing effective amount of a oligomeric tetramer of any of the compounds described herein.

Accordingly, an oligomeric tetramer of the compounds described herein is used for treating a medical condition associated with benign neoplastic tissue in a subject in need thereof.

In some embodiments, the oligomeric tetramer is a DPA tetramer as described herein.

In some embodiments, the method described herein is used for treating a medical condition associated with pre-malignant or malignant neoplastic tissue in a subject in need thereof, and is effected by administering to the subject a devitalizing effective amount of an oligomeric form of a compound, as described herein, wherein the oligomer comprises four or more monomeric units (e.g., the oligomer is a tetramer, pentamer or hexamer of DPA or any other compound as described herein).

Accordingly, oligomer forms of the compounds described herein, comprised of four or more monomeric units are used for treating a medical condition associated with pre-malignant or malignant neoplastic tissue in a subject in need thereof.

As exemplified in the Examples section that follows, both the monomeric and the tetrameric forms of DPA were effectively used to treat patients having benign tumors, viral warts or mucosal tumor lesions while longer oligomers were used to treat patients having malignant and pre-malignant tumors. All treatments resulted in eradication of the tumors with very good clinical outcomes (see, Table 10).

As discussed hereinabove, the present embodiments further encompass any pharmaceutically acceptable salts and complexes, as defined hereinabove, of the compounds described herein.

Without being bound by theory, it is speculated that the formation of complexes and salts may further enhance the devitalizing activity of the compounds described herein, possibly by constructing larger sized forms of the compound which, as discussed hereinabove, enable the selective penetration of the compound to the looser packed neoplastic tissue as compared to the penetration into the more densely packed normal tissue.

As discussed hereinabove, the beneficial therapeutic activity of DPA and oligomers thereof, as exemplary compounds according to embodiments of the invention, has been demonstrated in treating medical conditions associated with viral, benign, premalignant and malignant neoplastic tissues.

Accordingly, in any of the methods and uses described herein, the neoplastic tissue can be a viral neoplastic tissue, a benign neoplastic tissue, a pre-malignant neoplastic tissue and/or a malignant neoplastic tissue.

In some embodiments of the present invention, the neoplastic tissue is a skin or mucosal tissue.

The phrase "viral neoplastic tissue", as used herein, describes abnormal growth of tissue cells due to a viral infection.

The phrase "malignant neoplastic tissue", as used herein, describes a neoplastic tissue which is not self-limited in its growth, is capable of invading into adjacent tissues, and may be capable of spreading to distant tissues (metastasizing).

The phrase "benign neoplastic tissue" describes a neoplastic tissue which is not malignant (i.e. does not grow in an unlimited, aggressive manner, does not invade surrounding tissues, and most of them do not metastasize).

The phrase "premalignant neoplastic tissue" describes a neoplastic tissue which is not malignant but has a higher probability of becoming malignant as compared to normal tissue and benign neoplastic tissues.

The term "skin tissue" describes the outer covering of a mammalian form including, without limitation, the epidermis, dermis, and subcutaneous tissues. Typically, skin tissue can include other components such as hair follicles and sweat glands.

The term "mucosal tissue" describes tissues that are composed in part of cells of mesenchymal and epithelial origin. Examples of mucosal tissues include, but are not limited to, vaginal, oral, corneal, rectal, and viscero-elastic tissues.

The term "lesion" describes any abnormal tissue found on or in an organism, usually damaged by disease or trauma. The term "skin lesion" describes any abnormal tissue found on or in a skin tissue. The term "mucosal lesion" describes any abnormal tissue found on or in a mucosal tissue, as described herein.

The term "tumor" describes a swelling or lesion formed by an abnormal growth of pathologycal cells. The term "tumor" encompasses benign tumors (evolving from benign neoplastic tissue), pre-malignant tumors (evolving from premalignant neoplastic tissue) and malignant tumors which are also referred to herein as "metastasizing malignant tumors" (evolving from malignant neoplastic tissue).

The term "skin tumor" describes a tumor formed by an abnormal growth of skin cells. The term "skin cells" describes cells that make up the skin such as epidermal cells, dermal cells or cells making up the subcutaneous tissue of the skin. Some benign skin tumors are known to be caused by viruses (for example, warts), systemic disease (for example, xanthelasmas or xanthomas caused by excess fats in the blood), and environmental factors (for example, moles (nevi) and epidermal cysts stimulated by sunlight). Other examples of benign skin tumors are dermatofibromas; angiomas (such as hemangiomas, port-wine stains, lymphangiomas, and pyogenic granulomas); seborrheic keratoses; and acrochordons, or skin tags.

The term "mucosal tumor" describes a tumor formed by an abnormal growth of cells that make up mucosal tissue.

The term "cancer" describes a tumor formed by abnormal growth of malignant cells. The term cancer encompasses primary or secondary tumors. The term "primary tumor" describes a tumor that is at the original site where it first arose and the term "secondary tumor" describes a tumor that has spread from its original (primary) site of growth to another site, close to or distant from the primary site.

The term "skin cancer" describes a cancer located on or in a skin tissue and/or originating from the abnormal growth of skin cells. The term "mucosal cancer" describes a cancer located on or in a mucosal tissue and/or originating from the abnormal growth of cells that make up the mucosal tissue. There are several types of skin cancers, the most common being basal cell carcinoma and squamous cell carcinoma, which are both non-melanoma skin cancers. Benign (non-cancerous) skin tumors may be present at birth or develop later.

Accordingly, exemplary skin and mucosal neoplastic tissues include, but are not limited to, keratoses (including, but not limited to, actinic keratosis, hydrocarbon keratosis, keratosis pilaris, seborrheic keratosis), nevi (including melanocytic nevi and epidermal nevi, with exemplary nevus listed hereinunder), archodrons, cysts, angiomas (such as hemangiomas, port-wine stains, lymphangiomas, and pyogenic granulomas), fibromas, fibrolipomas, condylomatas, lentigos, acanthomas, neurofibromas, hyperplasias, fibromas, warts (caused, for example, by viruses, e.g., verrucas), leiomyomas, syringomas, granulomas, xanthelasmas, cutaneus horns, Juvinel pseudomelanoma, basal cell carcinomas, basaliomas, Squamous cell carcinomas, Merkel-trabecular cell carcinomas, Nevus sebaceus of Jadassohn with basal cell carcinoma, kaposis sarcomas, oral visible lesions, papillomas, ibroepitheliomas, hyperplasias, hypertrophic Lesions, polips, freckles, melasmas and melanomas.

Such neoplastic tissues are evolved from medical conditions such as, but not limited to, a viral infection (resulting in a viral neoplastic tissue), systemic disease (for example, xanthelasmas or xanthomas caused by excess cholesterol and fats in the blood), various types of skin cancers, and environmental factors (for example, moles (nevi) and epidermal cysts stimulated by sunlight.

Exemplary medical conditions that are associated with neoplastic tissues such as listed hereinabove and which are treatable by the compounds described herein include, but are not limited to, Seborrheic keratosis, Epidermal Nevus, Linear epidermal nevus (unius lateralis), Nevus sebaceus of Jadassohn, Intradermal Nevus, Nevus pilosus, Skin tags and acrochordons, Epidermal inclusion cysts, Sebaceous hyperplasia, Multiple syringomas, Clear cell acanthoma, Compound nevus, Halo Nevi, Spindle cell (Spitz) nevus (epitheloid), Giant Hairy Nevus, Blue Nevus, Nevus of Ota, Dermatofibroma, Angiofibroma, Multiple cherry hemangioma, Pyogenic granuloma, Angiokeratoma, Lymphangioma, Junctional Nevus, Nevus Araneus (Spider telangiectasia), Reclingausen disease (Neurofibromatisis), Steroide form Hyperkeratosis and Papillomatosis, Nevus vasculosus, Nevus depigmentasus, Nevus flammeus (Port-wine stain), Xanthelasma, Verruca vulgaris, Verruca plana, Condiloma acuminatum, Molluscum contagiosum, Actinic keratosis, Cutaneus horn, Bowens disease, Lentigo simplex and senilis, Lentigo maligna, Keratoacanthoma, Trychoepitheliomas, Multiple displastic Nevi, Arsenal keratosis, Juvinel pseudomelanoma, Superficial basal cell carcinoma, Basal cell carcinoma, Nodular basal cell carcinoma, Basal cell pigmented nevus syndrome-Basaliomas, Squamous cell carcinoma, Merkel-trabecular cell carcinoma, Nevus sebaceus of Jadassohn with basal cell carcinoma, Superficial spreading melanoma in situ and stage 1a, Nodullar malignant melanoma in situ and stage 1a, Kaposis hemorrhagic sarcoma (Early macular lesion, non-AIDS related), oral visible lesions, Lentigo malignant melanoma, Papillomas, Fibroepitheliomas, Hemangiomas and Hyperplastic or Hypertrophic Lesions, Neurofibromatosis-1 (Recklinghausen disease), Neurofibromatosis-2, Erosionen (ectopie), Polipus, Posthysterectomie, granuloma, Endocervicitis, cervical viral warts such as molluscus contagious and condiloma acuminate; nabothian cysts; Epistaxis (contact bleeding from erosion of cervix).

As discussed elaborately hereinabove, while surgical removal of the skin or mucosal tumor/lesion is frequently the treatment of choice, this option is non-optimal and suffers from many drawbacks which render it not applicable in all patients.

For example, surgical treatment is problematic in treating patients suffering from multiple tumors/lesions. In such patients, besides the poor cosmetic result, the surgical removal of all tumors/lesions may lead to excessive skin tension rendering surgical wound edge closure problematic. In such cases, the topical administration of the compounds described herein onto the multiple tumors/lesions is particularly beneficial due to the complete devitalization of the tumors/lesions with a very good therapeutic as well as cosmetic result.

Hence, in some embodiments, the medical condition is characterized by multiple skin and/or mucosal lesions.

An exemplary medical condition characterized by multiple skin tumors is peripheral Neurofibromatosis (Recklinghausen disease).

As further discussed hereinabove, there is an increase in occurrence of skin disorders characterized by skin neoplasia, such as skin lesions and skin cancer, caused by extensive exposure of the skin to irradiation such as ultraviolet beta rays.

Hence, in some embodiments the medical condition is caused by irradiation (e.g., sun irradiation and/or photoirradiation).

As exemplified in the Examples section that follows, the compounds described herein are capable of devitalizing neoplastic tissues located externally, namely skin and mucosal tissues. Since the pathophysiology associated with neoplastic skin and mucosal tissue is similar to the pathophysiology of all neoplastic tissues, the compounds of the present invention can be further utilized in the treatment of medical conditions associated with internal neoplastic tissues.

Thus, is some embodiments, the compounds described herein are administered for treating a medical condition associated with neoplastic tissue wherein the neoplastic tissue is an internal tissue.

The phrase "internal tissue" is used interchangeably herein with the phrase "intracorporeal tissue" and describes any tissue located in the body of a subject which is inaccessible externally. The phrase "internal tissue" encompasses any tissue other than skin and mucosal tissues, as described herein, that is, any tissue within the corpus.

The phrase "internal neoplastic tissue" describes an internal tissue, as defined herein, wherein neoplasia occurs. Non-limiting examples of internal neoplastic tissue include liver neoplastic tissue, thyroid neoplastic tissue, bile duct neoplastic tissue, bladder neoplastic tissue, bone neoplastic tissue, brain neoplastic tissue, breast neoplastic tissue, lung neoplastic tissue, gastrointestinal neoplastic tissue, colon neoplastic tissue, genital neoplastic tissue, epithelial neoplastic tissue, esophageal neoplastic tissue, kidney neoplastic tissue, pancreatic neoplastic tissue, ovarian neoplastic tissue, cervix neoplastic tissue, uterus neoplastic tissue, testicular neoplastic tissue, pancreatic neoplastic tissue, prostate neoplastic tissue, rectal neoplastic tissue, stomach neoplastic tissue, sweat gland neoplastic tissue, oral neoplastic tissue, ocular-retinal neoplastic tissue, muscular neoplastic tissue.

Non-limiting exemplary medical conditions associated with internal neoplastic tissue and treatable by the compounds described herein are solid malignant tumors such as, but not limited to, brain, ovarian, colon, prostate, kidney, bladder, breast, uterine, cervical and lung cancers. These cancers can be further broken down. For example, brain cancers include glioblastoma multiforme, anaplastic astrocytoma, astrocytoma, ependyoma, oligodendroglioma, medulloblastoma, meningioma, sarcoma, hemangioblastoma, and pineal parenchymal.

Non-limiting examples include, but are not limited to, acoustic neuroma, adenocarcinoma, angiosarcoma, astrocytoma, bile duct carcinoma, bladder carcinoma, thyroid cancer, tracheal cancer, bone originated tumor such as bone sarcoma, brain tumor such as glioma and neuroblastoma; breast cancer, cervical cancer, chondrosarcoma, chordoma, choriocarcinoma, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, hemangioblastoma, hepatic carcinoma, leiomyosarcoma, liposarcoma, lung carcinoma such as bronchogenic carcinoma, small cell lung carcinoma; lymphangioendotheliosarcoma, lymphangiosarcoma, medullary carcinoma, medulloblastoma, mesothelioma, myxosarcoma, pancreatic cancer, oligodendroglioma, osteogenic sarcoma, ovarian cancer, pancreatic carcinoma, papillary carcinoma, papillary adenocarcinoma, pinealoma, prostate cancer, rectal cancer, kidney cancer such as renal cell carcinoma and Wilms' tumor; retinoblastoma, rhabdomyosarcoma, sebaceous gland carcinoma, seminoma, stomach carcinoma, synovioma, sweat gland carcinoma, testicular tumor, uterus carcinoma, and metastatic disease of the respective primary cancer.

The administration of the compounds described herein may be effected either locally or via systemic administration. While the devitalizing effect of the compounds described herein may be achieved via directly contacting the neoplastic tissue with the compound, an indirect effect may also occur, for example, by enhancing the response of the immune system against neoplastic cells through a systemic route, as is detailed hereinunder.

In some embodiments, administering the compound is effected by contacting the neoplastic tissue with the compound.

In some embodiments, the administering is effected topically.

In some embodiments, the administering is effected incorporeally.

The term "topically" as used herein, describes the administration of the compounds described herein onto a surface of the body, such as a neoplastic skin or mucosal tissue.

The term "intracorporeally", as used herein, describes an administration which is effected within the body (as apposed to onto the body surface, i.e., topically). An intracorporeal administration encompasses the administration of the compounds described herein during a surgical procedure that enables the direct contact between the compound and internal neoplastic tissue which is otherwise inaccessible.

Non-limiting examples of intracorporeal administration include local, stereotactic and intravascular administration.

Local administration, as used herein, describes applying the compound directly onto the neoplastic tissue. Intracorporeal local administration describes applying the compound directly onto an internal neoplastic tissue, for example, during a surgical procedure. The term "local administration" encompasses also administration via intratumoral injection, namely injection of the drug directly into the tumor.

Stereotactic administration uses a computer and imaging performed in at least two planes to localize the target neoplastic tissue (such as a tumor) in three-dimensional space and guide the compound to the tissue. This includes, for example, an administration operated under "direct vision".

Intravascular administration, as used herein, describes the administration of the compound to the blood vessels of the neoplastic tissue.

For example, cervical and/or uterine neoplasms can be treated by topically applying the compounds or compositions described herein to the neoplastic tissue, by means of e.g., contacting the tissue with a sponge soaked with the compound.

Bladder carcinoma can be treated by administering the compound using the direct vision technique.

Abdominal neoplasia can be treated by local administration of the compound during a surgical procedure.

One of the important beneficial characteristics of the compounds described herein is that while the compounds devitalize the neoplastic tissue, the tissue is still suitable for histological evaluation, thereby enabling the physician to assess the specific histological characteristics of the tissue. Hence, in some embodiments, in any of the methods and uses described herein histologically evaluation of the neoplastic tissue is performed subsequent to the compound administration.

In some embodiments, the compounds described herein are utilized within a co-therapy, which further comprises surgically removing at least a portion of the neoplastic tissue. In such cases, the administration of the compound may be prior to, during or subsequent to the surgical procedure.

Administering the compound prior to the surgical procedure can be effected by any of the methods (routes of administrations) described herein. In some embodiments, the compound is administered locally before removal of the neoplastic tissue, yet during the surgical procedure.

Administering the compound subsequent to the surgical procedure can be effected either in vivo, subsequent to surgically removing the neoplastic tissue, or ex-vivo, where the compound is applied to the removed neoplastic tissue.

As discussed hereinabove, the surgical removal of neoplastic tissue is one of the treatment options frequently employed in the management of medical conditions associated with neoplastic tissue. However, when the neoplastic tissue is malignant, during the surgical manipulation, dissemination of malignant cells into the blood and lymph vessels may occur, resulting in metastasis in other body locations and postoperative recurrence. Therefore, treating such medical conditions with the compounds described herein is beneficial, as compared to a surgical treatment alone, since the dissemination which may occur and the risk of a secondary tumor evolving form metastasis is much lower. Support for such a statement is presented in the Examples section that follows. As shown therein, the level of malignant skin tumor recurrence following DPA or DPA oligomer treatment, during the 2-8 year follow-up period was negligible and furthermore, no occurrences of regional and distant metastases of the skin tumors as well as lethality cases were reported.

Hence, in some embodiments of the present invention, the method described herein is for treating a medical disorder which is associated with malignant neoplastic tissue, whereby the method being for reducing or abolishing dissemination of malignant cells into blood or lymph vessels. In some embodiments the dissemination of malignant cells is associated with a surgical procedure.

Accordingly, in accordance with another aspect of some embodiments the present invention, there is provided a method of reducing or abolishing dissemination of malignant cells into a blood and/or lymph vessel of a subject having a medical condition associated with malignant neoplastic tissue and subjected to a surgical procedure for removing at least a portion of the malignant neoplastic tissue. The method, according to this aspect of the invention, is effected by administering to the subject, prior to or concomitant with the surgical procedure, a devitalizing effective amount of a compound as described herein.

In accordance with another aspect of some embodiments of the present invention there is provided a use of a compound as described herein in the manufacture of a medicament for reducing or abolishing dissemination of malignant cells into a blood and/or lymph vessel of a subject having a medical condition associated with malignant neoplastic tissue and subjected to a surgical procedure for removing at least a portion of the malignant neoplastic tissue.

In some embodiments, the malignant neoplastic tissue is a skin or mucosal tissue. In some embodiments the malignant neoplastic tissue is an internal tissue as defined herein.

In some embodiments, the medical condition is a metastasizing malignant skin or mucosal tumor, as defined herein.

Non-limiting examples of malignant skin and mucosal medical conditions in which a surgical procedure is used for removal of the malignant neoplastic skin or mucosal tissue and which are suitable for treatment by the compounds described herein are Superficial basal cell carcinoma, Basal cell carcinoma, Nodular basal cell carcinoma, Basal cell pigmented nevus syndrome-Basaliomas, Squamous cell carcinoma, Merkel-trabecular cell carcinoma, Nevus sebaceus of Jadassohn with basal cell carcinoma, Superficial spreading melanoma in situ and stage 1a, Nodullar malignant melanoma in situ and stage 1a, Kaposis hemorrhagic sarcoma (Early macular lesion, non-AIDS related) and Lentigo malignant melanoma.

Non-limiting examples of malignant medical conditions in which a surgical procedure is used for removal of internal neoplastic tissue and are suitable for treatment by the compounds described herein are solid malignant tumors as described herein, including, but not limited to, acoustic neuroma, adenocarcinoma, angiosarcoma, astrocytoma, bile duct carcinoma, bladder carcinoma, thyroid cancer, tracheal cancer, bone originated tumor such as bone sarcoma, brain tumor such as glioma and neuroblastoma; breast cancer, cervical cancer, chondrosarcoma, chordoma, choriocarcinoma, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, hemangioblastoma, hepatic carcinoma, leiomyosarcoma, liposarcoma, lung carcinoma such as bronchogenic carcinoma, small cell lung carcinoma; lymphangioendotheliosarcoma, lymphangiosarcoma, medullary carcinoma, medulloblastoma, mesothelioma, myxosarcoma, pancreatic cancer, oligodendroglioma, osteogenic sarcoma, ovarian cancer, pancreatic carcinoma, papillary carcinoma, papillary adenocarcinoma, pinealoma, prostate cancer, rectal cancer, kidney cancer such as renal cell carcinoma and Wilms' tumor; retinoblastoma, rhabdomyosarcoma, sebaceous gland carcinoma, seminoma, stomach carcinoma, synovioma, sweat gland carcinoma, testicular tumor, uterus carcinoma, or metastatic disease of the respective primary cancer.

In any of the methods and uses described herein, the compounds as defined herein can be utilized in combination with an additional active agent. An exemplary such additional active agent is a selenium-containing agent. The ant-cancer activity of selenium and selenium containing compounds has been previously reported [Clark et al. *Nutr Cancer.* 2008; 60(2):155-63]. For example, $SeO_2$ has been known to increase concentration of the endogenic antioxidant glutathione. Selenium containing compounds such as $SeO_2$ have also been known to be immunostimulants, as well as to inhibit tumor growth and dissemination. It is therefore, suggested that the co-administration of selenium or a compound which comprises selenium together with the halogenated aliphatic acids described herein can achieve an enhanced devitalizing effect.

In some embodiments, the selenium-containing is a selenium salt, a selenium oxide, a selenium halide or a selenium acid. Exemplary selenium-containing which are suitable for use in the context of the present embodiments include, but are not limited to, $SeH_4$, $SeCl_4$, $SeF_4$, $SeOCl_2$, $SeH_2O_4$ or $SeH_2O_3$.

In some embodiments, any of the methods and uses described herein, the compound is administered between 1 to 10 times during the treatment period. In some embodiments, the compound is administered once or twice during the treatment period. By "treatment period" it is meant the time period required for abolishing or reducing the neoplastic tissue and/or the time period after which no recurrence of the neoplastic tissue is observed.

Without being bound by theory, it is speculated that the compounds described herein devitalize malignant and premalignant neoplastic tissue located in a primary tumor so as to release antigenic components of these malignant and premalignant cells into the blood and lymph vessels, thereby enabling the immune system to recognize these antigens and exert a direct or indirect immune response to these antigens. This induced immune response can subsequently lead to the identification of similar antigens, located on malignant cells at the primary tumor site as well as malignant cells that have disseminated from the primary tumor into the blood/lymph vessels, and destroy these cells, thereby inhibiting the growth of the tumor and reducing the ability of the malignant tumor to metastasize and create a secondary tumor.

Hence, according to another aspect of some embodiments of the present invention, there is provided a method of inducing a systemic immune response to malignant cells, the method comprising administering to a subject in need thereof a therapeutically effective amount of a compound as described herein.

Accordingly, according to another aspect of some embodiments of the present invention there is provided a use of a compound as described herein in the manufacture of a medicament for inducing a systemic immune response to malignant cells.

The induction of the immune response can be further utilized in order to reduce the capability of premalignant cells and/or potentially malignant cells to become malignant by destroying these cells through, the recognition of their antigenic components, before they are transformed into malignant type cells.

Thus, according to another aspect of some embodiments of the present invention, there is provided a method of inducing a systemic immune response to pre-malignant, and/or potentially malignant cells, the method comprising administering to a subject in need thereof a therapeutically effective amount of a compound as described herein.

Accordingly, according to another aspect of some embodiments of the present invention there is provided a use of a compound as described herein in the manufacture of a medicament for inducing a systemic immune response to pre-malignant, and/or potentially malignant cells.

The phrase "malignant cell" describes a neoplastic cell which is not self-limited in its growth, is capable of invading into adjacent tissues, and may be capable of spreading to distant tissues (metastasizing).

The phrase "premalignant cell" and "potentially malignant cell" are used interchangeably to describe a cell which is not malignant but has a higher probability of becoming malignant as compared to a normal cell.

The phrase "systemic immune response" describes the whole body production and circulation, upon exposure to an antigen, of organism specific humoral and cellular immune cells and is characterized by organism specific immune globulin (antibodies) and cytotoxic mononuclear cells. As used herein, an "antigen" may be any substance which, when introduced into a mammal, will induce a detectable immune response, both humoral and cellular. As used herein, the term "antigen" also includes any portion of an antigen, e.g., the epitope, which can induce an immune response.

In some embodiments the induced systemic immune response is an innate immune response or an acquired immune response.

The immune system of higher organisms is comprised of an adaptive (acquired) and an innate component. The innate immune system refers to a host's antigen-nonspecific defense mechanisms that come into action immediately or within several hours after exposure to almost any antigen. The innate immune system represents the initial response by the body to eliminate microbes. The innate immune system includes phagocytic cells, which includes macrophages and polymorphonuclear leukocytes that can engulf (phagocytose) foreign substances. By contrast, the adaptive immune system refers to antigen-specific defense mechanisms that emerge over several days, and react with and remove a specific antigen. The adaptive immune system develops throughout a lifetime. The adaptive immune system is based on leukocytes, and is divided into two major sections: the humoral immune system, which acts mainly via immunoglobulins produced by B cells, and the cell-mediated immune system, which functions mainly via T cells.

The induction of a systemic immune response may be effected by upregulating an expression of an endogenous factor such as TNF-α, Interferon-α, Interleukin-1, Interleukin-5, Interleukin-6 and Interleukin-8 and a combination thereof. The induction may be further effected via the activation of T helper cells type −1. The induction may be further effected via activation of a cytokine such as interferon, IL-10 or IL-12.

The induction of a systemic immune response by the compounds described herein may be further enhanced by the co-administration of the compound together with an immunostimulating agent.

Hence, in some embodiments, the compounds described herein are utilized in combination with at least one immunostimulating agent.

The term "immunostimulating agent" describes a compound which stimulates the immune response of a subject. Exemplary immunostimulating properties can be manifested, for example, by an effect on cytokines secretion, interleukins production, lymphocytes function, and the like. In some embodiments, the immunostimulating agent is Granulocyte-macrophage colony-stimulating factor (GM-CSF).

Additional exemplary immunostimulants include, but are not limited to, recombinant human interleukin 2 (rIL-2), polysaccharides of mannose (e.g. mannans), β(1,3) glucose (e.g. glucans), β(1,4) acetylated mannose (acemannans), β(1,4) N-acetyl-glucosamine (chitins), heteropolysaccharides, such as rhamnogalacturonans (pectins), water-soluble polymers, muramyl peptides, lipopolysaccharides (LPS) from gram-negative bacteria and derivatives thereof, and any other of cationic detergents, interleukins, interferons and growth factors.

The devitalizing activity of the compounds described herein may be further due to the ability of the compounds to inhibit angiogenesis in neoplastic tissue thereby reducing the blood supply to the tissue. The inhibition of angiogenesis may be effected via downregulating the expression of proangiogenic factors or/and upregulating the expression of an endogenous angiogenesis inhibitors such as endostatin, tumstatin, interferon, interleukin, and/or thrombospondin.

The devitalizing activity of the compounds described herein may be further due to the ability of the compounds to induce an inflammatory response to pre-malignant, malignant and/or potentially malignant cells. The inflammatory response may be effected via upregulating the expression of inflammatory chemoattractant proteins.

In any of the methods and uses described herein, the compounds described herein can be utilized either per se or being formulated into a pharmaceutical composition which may further comprise a pharmaceutically acceptable carrier.

Thus according to some embodiment of the present invention the compound forms a part of a pharmaceutical composition which further comprises a pharmaceutically acceptable carrier.

According to another aspect of some embodiments of the invention there is provided a pharmaceutical composition comprising, as an active ingredient, any of the compounds described herein, and a pharmaceutically acceptable carrier.

According to another aspect of some embodiments of the present invention there is provided a use of any of the compounds as described herein in the manufacture of a medicament.

According to another aspect of some embodiments of the invention there is provided a pharmaceutical composition which comprises, as an active ingredient, the oligomers described herein (oligomer forms of a compound as described herein) and a pharmaceutically acceptable carrier.

According to another aspect of some embodiments of the present invention there is provided a use of an oligomer as described herein in the manufacture of a medicament.

In some embodiments the concentration of the compound in the composition ranges from 20 weight percents to 100 weight percents of the total weight of the composition, and can be 20, 30, 40, 50, 60, 70, 80, 90 or 100 weight percents of the composition, including any value therebetween. In some embodiments the concentration of the compound ranges from 70 weight percents to 90 weight percents of the total weight of the composition.

In some embodiments, the pharmaceutical composition further comprises at least one additional active agent, as described herein (e.g., a selenium-containing agent). In some embodiments, the pharmaceutical composition further comprises an immunostimulating agent as described herein.

In some embodiments, the pharmaceutical composition is packaged in a packaging material and identified in print, in or on the packaging material, for use in the treatment of a medical condition associated with a neoplastic tissue.

In some embodiments, the pharmaceutical composition is identified for use in reducing or preventing dissemination of malignant cells into a blood and/or lymph vessel of a subject having a medical condition associated with malignant neoplastic tissue and subjected to a surgical procedure for removing at least a portion of the malignant neoplastic tissue.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. As discussed hereinabove, while the therapeutic effect of the composition described herein may be achieved via directly contacting the neoplastic tissue with the compositions, an indirect effect may also occur for example, by enhancing the response of the immune system against the neoplastic cells through a systemic rout.

Therefore, in some embodiments the pharmaceutical composition or the medicament is formulated for topical administration. In some embodiments the pharmaceutical composition or the medicament is formulated for systemic administration.

In some embodiments the pharmaceutical composition or the medicament is formulated for incorporeal administration as defined herein.

Administration may be done, orally, by inhalation, or parenterally, for example by intravenous drip or intraperitoneal, subcutaneous, intramuscular or intravenous injection, stereotacticly, intravascular, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The composition may be formulated for application on to a neoplastic tissue during a surgical procedure. In such a case the formulation may be formulated so as to be suitable for local administration, intravascular administration or for use in a stereotactic procedure.

The amount of a composition to be administered will, of course, be dependent on the subject being treated, the severity of the affliction, the manner of administration, the judgment of the prescribing physician, etc.

Determination of the amount of composition to be administered onto the neoplastic tissue is well within the capability of those skilled in the art, especially in light of the detailed disclosure provided herein.

In some embodiments, the amount ranges from 0.001 ml to 5 ml of the composition per a neoplastic tissue diameter of 1 cm.

In some embodiments, the amount ranges from 0.01 ml to 1 ml of the composition per a neoplastic tissue diameter of 1 cm.

Thus, for example, an amount of 0.1 ml can be used to treat a neoplastic tissue having a diameter of 2-3 cm. An amount of 2 ml of the composition can be used to treat a neoplastic tissue having a diameter of 5-10 cm.

It is noted in this regard that, by being commonly used as a water disinfectant, 0.2 ml of DPA are added to 1 liter of water. Thus, it is appreciated that the above-indicated amounts are non-toxic and are within the doses orally consumed by any person that drinks disinfected water.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising the compound(s)/oligomers of the invention formulated in a compatible pharmaceutical carrier may also be prepared, placed in an appropriate container, and labeled for treatment of a medical condition associated with neoplastic tissue or for reducing or preventing dissemination of malignant cells into a blood and/or lymph vessel of a subject having a medical condition associated with malignant neoplastic tissue and subjected to a surgical procedure for removing at least a portion of the malignant neoplastic tissues as detailed hereinabove.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Chemical Syntheses

Materials, Syntheses and Methods:
DPA was obtained from Sigma-Aldrich Ag, as a colorless, transparent, slightly viscose, liquid substance. DPA of lower purity was also obtained from known vendors and was successfully used without further purification.

Selenium and Selenium Dioxide were obtained from MERCK Ag.

DPA can be reproduced in non-limited quantities with chemoanalytical and biological (efficacy) stability during at least 5 years, when stored in sealed brown glass containers at a temperature of between −4° C. and +50° C.

Synthesis of DPA in a Form of Tetraoligomer-Polymer(s):

A 70% (v/v) solution of DPA in water was heated to a temperature of 190° C., refluxed for 2, 4 or 6 hours, and cooled to room temperature. The obtained product was filtered, sonicated three times (an hour every day, for three consecutive days), using a Magnetostrictive Ultrasound Generator (USR), and filtered once again to yield a brown colored liquid.

Elemental analysis of the obtained products indicated that following a reflux period of 2 hours a dimmer of DPA was obtained; following a reflux time period of 4 hours a tetramer of DPA was obtained and following a reflux time period of 6 hours a longer oligomer of DPA was obtained.

The obtained oligomers are identified as lipophilic, with a tendency to form liposomes or nonvisible vesicles in aqueous solution.

Synthesis of a DPA Oligomer Complexed with Metallic Selenium:

Metallic Selenium (100 mg) was placed in a 250 ml pear shaped quartz glass flask and a DPA oligomer (100 ml, synthesized as described hereinabove) was carefully added thereto. The obtained suspension was refluxed for 6 hours at a temperature of 195° C. and then allowed to cool to room temperature. The resulting mixture was filtered, yielding the desired DPA oligomer-Selenium complex as a dark brown colored liquid.

Synthesis of a DPA Oligomer Complexed with Metallic Selenium and $SiO_2$:

A DPA oligomer-Selenium complex, synthesized as described hereinabove, and 10 ml of a 10% w/v aqueous solution of $SeO_2$ were mixed together. The mixture was sonicated (an hour every day for three consecutive days) and the product was thereafter filtered in order to discard off solid impurities. The resulting liquid was subjected to additional sonication cycles (an hour every day for three consecutive days) and was thereafter further filtered, yielding the desired product as a dark brown colored liquid.

Generally, in the Examples provided below, solutions containing either DPA, a DPA oligomer or a DPA oligomer complexed with selenium as described herein, were used. These are all referred to collectively as "DPA or a DPA oligomer".

Example 1

The Therapeutic Effect of DPA in Treating Various Skin Pathologies

Protocol:

6938 patients suffering from various skin pathologies, from different clinics, hospitals and private practices were recruited prospectively, and treated with DPA or an oligomer thereof synthesized as described hereinabove, under a common approved protocol.

Patients suffering from benign tumors, viral warts or mucosal membraneus tumors were administered with the tetramer form of DPA. In some cases, DPA, as a monomer, was used. Patients suffering from premalignant or malignant tumors were administered with longer oligomers of DPA.

In most cases, the DPA monomer or oligomer was administered only once and without anesthesia or other special conditions. Only in cases of patients suffering from Recklinghausen disease (a multiple form of peripheral Neurofibromatosis), when the number of skin tumor lesions was more than 100, multiple treatment sessions were performed.

Biopsy specimens of the skin tumors were taken immediately after the DPA oligomer treatment (after the full devitalization of the lesion tissue) by intravital fixation using radio-electrocauterization techniques, thereby avoiding lymphohematogenic dissemination of malignant cells from the tumor.

Safety Studies:

The safety of DPA oligomer treatment was assessed by evaluating the treated skin lesion appearance, local skin reaction, vital sign measurements, adverse events and concomitant medications taken by the patient.

Therapeutic Efficacy:

The efficacy of DPA oligomer in the treatment of the various skin pathologies was further examined by a short and long term follow-up.

Short Term Follow-Up:

All necessary, additional tests for further characterizing the skin lesion/tumor and detecting regional and distant metastasis (such as X-ray, biopsy and other laboratory tests) were performed in the medical institutions where the patient was insured.

At the 3-week, 6-week and 12-week post-treatment visit(s), a clinical assessment was performed to determine whether treated lesions were visible at the target site. Pigmented lesions, suspected of being malignant, were further evaluated microscopically by the excision of a biopsy sample with a 3 mm margin from the lesion, using the radioelectro technique, and histopathologically examining the sample for evidence of residual or recurrence of tumor.

Long Term Follow-Up:

Out of the 6,938 patients participating in the clinical trial, long term clinical outcomes for 4,778 of the patients (68.8%) was further obtained. The long term results were recorded for patients treated with DPA oligomer, 4-8 years following treatment. The 4,778 patients enrolled in the follow-up suffered from a total of 45,474 tumor lesions. 84% (4,021) of the patients had more than one tumor lesion and 8.4% (411) of the patients suffered from more than 100 malignant and non-malignant tumor lesions before treatment. 14% (6,524) of the tumor lesions were post-treatment local recurrences (after surgery, X-ray, laser, photo-, chemo-, immuno-manipulations, etc.).

The lesion pathology was determined microscopically in 1996 of the cases (both benign and malignant).

The long term follow-up included examination of local recurrences or asymptomatic regional and distant metastases, as well as the development of new primary lesions. Although no strict guidelines regarding the number of follow-up sessions were determined, each patient was reexamined at least 3 times per year, with the exact number of reexaminations depending on medical considerations such as the type of treated tumor and other risk factors such as family history of melanoma, patient anxiety or the patients ability to recognize signs and symptoms of the disease.

Patients treated for pigmented tumors were also monitored by the regional physician (in charge of routine physical and work-related medical examinations). In some cases, for example, for patients having malignant melanomas, histological assessment of the presence differentiation markers of melanocytes, including Protein-1 (TRP-1), S-100 and HMB-45, typically lacking when malignant melanoma occurs, was performed.

A visual assessment and video-photo of the target tumor area in each patient was performed at each follow-up meeting.

Statistical evaluation: The results of the long term follow-up were assessed using the intention to treat (ITT) analysis taking into account all 6938 patients.

Clinical Results

Therapeutic Efficacy:
Short-Term Follow-Up:
The short term clinical results of the DPA oligomer treatment were similar in all treated patients.
Long-Term Follow-Up:
The results of the DPA oligomer clinical trials are presented in Tables 1-11. Tables 1-5 present all of the 4,778 patient details subdivided according to the various types of benign (Table 1), viral (Table 2), pre-malignant (Table 3), non-metastasizing malignant (Table 4) and visible mucosal (Table 5) tumor lesions treated.

Table 6 presents a summary of the number of patients and tumors in each category which were further reexamined in the long term follow-up. Table 7 presents data regarding the age of the patients and Table 8 presents data regarding the follow-up time length. Table 9 presents data regarding the level of definitive clinical diagnosis of the type of tumor using biopsy and histological examination and/or cytological examination and/or only clinical examination.

Table 10 presents the clinical results of the efficacy of the DPA administration during the 2-8 years follow-up period with very good clinical results observed in 82.1% of the tumors and a satisfactory level of clinical results observed in 99.1% of the tumors.

Table 11 presents data showing the level of tumor recurrence following DPA oligomer treatment during the 2-8 years follow-up period. The results show that the recurrent level of all tumor types was very low with the percentage of recurrence being only 2.3%, 6.1%, 3.5%, 2.8% and 1.2% for benign, viral, pre-malignant, non-metastasizing malignant and mucosal tumors, respectively.

No occurrences of regional and distant metastases of the skin tumors as well as lethality cases were reported.

The results show that the high efficacy of DPA oligomer treatment was observed in all treated skin tumor or lesion and was not dependent on the type of tumor/lesion, age, skin color or gender of the patient. The only exception was plantar and palmar hyperkeratotic warts in which case a cure rate of only 10% was observed. It is well-known that such lesions are highly resistant and should be recognized that such a cure rate is significant with respect thereto.

With regard to the safety of treatment with DPA oligomer, a short term local allergic reaction, pain and itching were observed in 5.8% of the patients during the treatment period, with a possible development of visible skin hypo- or hyper-pigmentation, as well as scar and kelloid formation. No systemic toxicity was detected in any of the patients.

In conclusion, the results show that DPA oligomer treatment is a highly effective drug for use in the treatment of viral, benign, premalignant and non-metastasizing malignant skin and mucosal tumors and lesions.

TABLE 1

| Benign Skin tumors | No of patients | No of lesions | Sex Male | Sex Female | Skin color Fair | Skin color Dark | Length of Follow-up (months) Range | Length of Follow-up (months) Mean | Post treatment scars (%) |
|---|---|---|---|---|---|---|---|---|---|
| Seborrheic keratosis | 452 | 3824 | 302 | 150 | 184 | 268 | 6-51 | 34 | 3.4 |
| Epidermal Nevus | 196 | 528 | 112 | 84 | 134 | 62 | 13-74 | 52 | 12.1 |
| Linear epidermal nevus (unius lateralis) | 32 | 53 | 19 | 13 | 17 | 15 | 24-78 | 56 | 5.2 |
| Nevus sebaceus of Jadassohn | 58 | 84 | 33 | 25 | 40 | 18 | 15-62 | 41 | 4.9 |
| Intradermal Nevus | 294 | 1053 | 157 | 137 | 188 | 106 | 3-86 | 59 | 6.7 |
| Nevus pilosus | 36 | 78 | 22 | 14 | 21 | 15 | 5-74 | 44 | 1.5 |
| Skin tags and acrochordons | 114 | 2188 | 76 | 38 | 70 | 44 | 5-96 | 71 | 1.8 |
| Epidermal inclusion cysts | 47 | 158 | 15 | 92 | 18 | 29 | 16-72 | 52 | 0.0 |
| Sebaceous hyperplasia | 95 | 884 | 30 | 65 | 55 | 40 | 8-64 | 47 | 0.1 |
| Multiple syringomas | 44 | 615 | 7 | 37 | 12 | 32 | 11-73 | 42 | 1.2 |
| Clear cell acanthoma | 110 | 214 | 73 | 37 | 71 | 39 | 14-62 | 38 | 13.1 |
| Compound nevus | 97 | 436 | 61 | 36 | 50 | 47 | 10-85 | 54 | 4.7 |
| Halo Nevi | 27 | 31 | 18 | 9 | 8 | 19 | 11-64 | 47 | 14.2 |
| Spindle cell (Spitz) nevus (epitheloid) | 104 | 380 | 56 | 48 | 38 | 66 | 14-92 | 70 | 6.4 |
| Giant Hairy Nevus | 18 | 34 | 5 | 13 | 7 | 11 | 6-87 | 61 | 12.3 |
| Blue Nevus | 116 | 429 | 29 | 87 | 34 | 82 | 15-74 | 52 | 8.8 |
| Nevus of Ota | 5 | 5 | 2 | 3 | 1 | 4 | 7-52 | 34 | 7.1 |
| Dermatofibroma | 88 | 202 | 34 | 54 | 38 | 50 | 12-76 | 48 | 3.6 |
| Angiofibroma | 129 | 156 | 81 | 48 | 49 | 80 | 8-72 | 44 | 1.0 |
| Multiple cherry hemangioma | 24 | 412 | 8 | 16 | 17 | 7 | 13-92 | 63 | 1.3 |

TABLE 1-continued

| Benign Skin tumors | No of patients | No of lesions | Sex Male | Sex Female | Skin color Fair | Skin color Dark | Length of Follow-up (months) Range | Length of Follow-up (months) Mean | Post treatment scars (%) |
|---|---|---|---|---|---|---|---|---|---|
| Pyogenic granuloma | 44 | 67 | 31 | 13 | 19 | 25 | 8-84 | 51 | 0.9 |
| Angiokeratoma | 184 | 498 | 80 | 104 | 97 | 87 | 6-79 | 52 | 0.1 |
| Lymphangioma | 12 | 36 | 5 | 7 | 7 | 5 | 11-68 | 48 | 0.4 |
| Junctional Nevus | 106 | 112 | 61 | 45 | 40 | 66 | 13-88 | 51 | 12.2 |
| Nevus Araneus (Spider telangiectasia) | 23 | 106 | 13 | 10 | 16 | 7 | 6-75 | 46 | 0.1 |
| Reclingausen disease-Neurofibromatisis | 28 | 1236 | 20 | 8 | 15 | 13 | 18-64 | 50 | 1.2 |
| Steroide form Hyperkeratosis and Papillomatosis | 30 | 1158 | 12 | 18 | 21 | 9 | 9-76 | 53 | 2.4 |
| Nevus flammeus (Port-wine stain) | 8 | 8 | 6 | 2 | 3 | 5 | 13-82 | 42 | 0.2 |
| Xanthelasma | 103 | 397 | 30 | 73 | 66 | 37 | 5-90 | 61 | 1.9 |
| Total | 2624 | 15282 | 1398 | 1286 | 1336 | 1288 | | | |

TABLE 2

| Viral warts | No of patients | No of Tumors | Gender Male | Gender Female | Skin color Fair | Skin color Dark | Length of Follow-up (months) Range | Length of Follow-up (months) Mean |
|---|---|---|---|---|---|---|---|---|
| Verruca vulgaris | 104 | 957 | 60 | 44 | 74 | 30 | 6-84 | 60 |
| Verruca plana | 52 | 1017 | 31 | 21 | 24 | 28 | 6-71 | 52 |
| Verruca palmaris and plantaris | 98 | 438 | 54 | 44 | 59 | 39 | 11-68 | 42 |
| Condiloma acuminatum | 78 | 241 | 60 | 18 | 54 | 24 | 6-91 | 59 |
| Molluscum contagiosum | 41 | 827 | 28 | 13 | 27 | 14 | 9-84 | 47 |
| Total | 373 | 3480 | 233 | 140 | 238 | 135 | | |

TABLE 3

| Premalignant tumors | No of patients | No of tumors | Gender Male | Gender Female | Skin color Fair | Skin color Dark | Length of Follow-up (months) Range | Length of Follow-up (months) Mean |
|---|---|---|---|---|---|---|---|---|
| Actinic keratosis | 233 | 2612 | 181 | 52 | 199 | 34 | 5-78 | 52 |
| Cutaneus horn | 84 | 216 | 56 | 28 | 58 | 26 | 9-81 | 54 |
| Bowens disease | 51 | 327 | 32 | 19 | 37 | 14 | 6-94 | 42 |
| Lentigo simplex and senilis | 102 | 498 | 68 | 34 | 71 | 31 | 3-87 | 50 |
| Lentigo maligna | 102 | 232 | 66 | 36 | 71 | 31 | 14-92 | 68 |
| Keratoacanthoma | 84 | 114 | 62 | 22 | 59 | 25 | 7-83 | 51 |
| Trychoepitheliomas | 32 | 217 | 21 | 11 | 19 | 13 | 6-74 | 44 |
| Multiple displastic Nevi | 52 | 288 | 28 | 24 | 31 | 21 | 6-98 | 60 |
| Arsenal keratosis | 2 | 32 | — | 2 | 2 | — | 11-68 | 41 |
| Juvinel pseudomelanoma | 4 | 16 | 3 | 1 | 2 | 3 | 14-77 | 47 |
| Total | 746 | 455 | 517 | 229 | 549 | 198 | | |

TABLE 4

| Malignant skin tumors | No of patients | No of tumors | Gender | | Skin | | Length of Follow-up (months) | | Post treatment scars (%) |
|---|---|---|---|---|---|---|---|---|---|
| | | | Male | Female | Fair | Dark | Range | Mean | |
| Superficial basal cell carcinoma | 148 | 315 | 88 | 60 | 111 | 37 | 3-98 | 67 | 3.7 |
| Basal cell carcinoma | 498 | 2024 | 301 | 197 | 318 | 180 | 3-81 | 53 | 8.1 |
| Nodular basal cell carcinoma | 102 | 381 | 73 | 29 | 60 | 480 | 6-78 | 47 | 11.2 |
| Basal cell pigmented nevus syndrome-Basaliomas | 18 | 190 | 11 | 7 | 13 | 5 | 8-92 | 43 | 6.2 |
| Squamous cell carcinoma | 98 | 422 | 68 | 30 | 59 | 1 | 33-90 | 44 | 14.3 |
| Merkel-trabecular cell carcinoma | 4 | 27 | 1 | 3 | 3 | 1 | 14-74 | 53 | 6.6 |
| Nevus sebaceus of Jadassohn with basal cell carcinoma | 47 | 144 | 29 | 18 | 33 | 14 | 6-80 | 48 | 1.4 |
| Superficial spreading melanoma in situ and stage 1a | 5 | 11 | 3 | 2 | 4 | 1 | 18-75 | 41 | 2.8 |
| Nodullar malignant melanoma in situ and stage 1a | 3 | 3 | 2 | 1 | 3 | — | 11-83 | 48 | 6.8 |
| Kaposis hemorrhagic sarcoma (Early macular lesion, non-AIDS related) | 15 | 157 | 8 | 7 | 11 | 4 | 13-67 | 35 | 1.4 |
| Lentigo malignant melanoma | 57 | 85 | 33 | 24 | 41 | 16 | 3-92 | 62 | 8.2 |
| Total | 995 | 3759 | 617 | 378 | 656 | 739 | | | |

TABLE 5

| Mucus membrane tumors (oral) | No of patients | No of tumors | Gender | | Skin color | | Length of Follow-up (months) | | Post treatment scars (%) |
|---|---|---|---|---|---|---|---|---|---|
| | | | Male | Female | Fair | Dark | Range | Mean | |
| Papillomas | 98 | 306 | 44 | 54 | 35 | 63 | 8-84 | 56 | 0.1 |
| Fibroepitheliomas | 16 | 44 | 12 | 4 | 8 | 8 | 6-77 | 49 | 2.3 |
| Hemangiomas | 4 | 13 | 3 | 1 | 2 | 2 | 14-82 | 51 | 1.9 |
| Hyperplastic or Hypertrophic Lesions | 22 | 38 | 16 | 6 | 7 | 19 | 10-78 | 42 | 0.9 |
| Total | 140 | 401 | 75 | 65 | 52 | 88 | | | |

TABLE 6

| Type of lesions | Number of patients | % | Number of Tumors | % |
|---|---|---|---|---|
| Benign Tumors | 2524 | 52.8 | 13,182 | 52 |
| Viral warts | 373 | 7.8 | 3,480 | 13.7 |
| Premalignant tumors | 746 | 15.7 | 4,552 | 17.9 |
| Malignant skin tumors (nonmetastasizing) | 995 | 20.8 | 3,759 | 14.8 |
| Mucosal membraneus tumors | 140 | 2.9 | 401 | 1.6 |
| Total | 4778 | 100 | 25,374 | 100 |

TABLE 7

| Range of Age | Number of patients |
|---|---|
| 1-10 | 121 |
| 11-20 | 384 |
| 21-30 | 401 |
| 31-40 | 1553 |
| 41-50 | 528 |
| 51-60 | 1101 |
| 61-70 | 1180 |
| 71-80 | 342 |
| 81-90 | 198 |
| Total | 4778 |

TABLE 8

| Months | Patients |
|---|---|
| 5 | 0 |
| 5-10 | 41 |
| 11-15 | 124 |
| 16-20 | 104 |
| 21-25 | 255 |
| 26-30 | 381 |
| 31-35 | 227 |
| 36-40 | 315 |
| 41-45 | 891 |
| 46-50 | 688 |
| 51-55 | 711 |
| 56-60 | 467 |
| 60 | 574 |
| Total | 4778 |

TABLE 9

| Type of tumors and number of patients | Biopsy and histological Examination | | Cytological examination | | Only clinical examinations | |
|---|---|---|---|---|---|---|
| | No of patients | % | No of patients | % | No of patients | % |
| Benign Tumors (2524 patients) | 754 | 29.9 | 520 | 20.6 | 1,250 | 49.5 |
| Viral warts (373 patients) | 14 | 3.7 | 22 | 5.9 | 337 | 90.4 |
| Premalignant Lesions (995 patients) | 438 | 44 | 256 | 34.3 | 208 | 21.7 |
| Malignant Tumors | 786 | 79 | 148 | 14.9 | 209 | 6.1 |
| Mucosal membraneus (140 patients) | 4 | 2.8 | 39 | 27.8 | 97 | 69.1 |
| Total All together 3089 | 1996 | 41.8 | 1,093 | 22.9 | 2,198 | 46 |

TABLE 10

| Type of tumor | Very good result (++++) % | Good results (+++) % | Satisfactory results (++) % | Poor results |
|---|---|---|---|---|
| Benign | 81 | 12.3 | 5.9 | 0.8 |
| Viral warts | 80.7 | 7.3 | 9.2 | 2.8 |
| Premalignant | 88.9 | 3.6 | 7.5 | — |
| Malignant | 76.0 | 17.2 | 6.7 | 0.1 |
| Mucosal membraneus | 82.4 | 11.9 | 5.3 | 0.4 |
| Total in % | 82.1 | 10.2 | 6.9 | 0.9% |

TABLE 11

| Type of tumors | Number of tumors = 25 374 | % | Number of recurrences of treated tumors | % | Number of recurrent tumors Retreated again | % |
|---|---|---|---|---|---|---|
| Benign Tumors | 15,282 | 52 | 315 | 2.3 | 255 | 80.9 |
| Virual warts | 3,480 | 13.7 | 213 | 6.1 | 202 | 95 |
| Premalignant lesions | 4,552 | 17.9 | 161 | 3.5 | 155 | 95 |
| Malignant Tumors | 3,759 | 14.5 | 107 | 2.8 | 99 | 92.5 |
| Mucosal membraneus | 401 | 1.6 | 5 | 1.2 | 5 | 100 |
| Cure rate 98.2% | | | | | | |

Example 2

Toxicology and Immunology Studies in Rats

Studies were conducted in order to evaluate the effect of administration of DPA or a DPA oligomer to rats. 1% and 0.1% (by weight) of a solution of DPA or an oligomer thereof were used, and the solution was administered daily for several days. The obtained data (not shown) showed that none of the rats demonstrated morphological changes in any of the tissues that are responsible for immunological responses nor were there abnormalities in the generation of IgM expressed as CPP-Ig million after several days of daily use of the tested solution.

Example 3

The Therapeutic Effect of DPA in Treating Various Skin Pathologies

In additional clinical trials, patients suffering from various skin pathologies were recruited, and treated with DPA or an oligomer thereof synthesized as described hereinabove, under a common approved protocol.

Patients suffering from benign, pre-malignant and malignant tumors, viral warts or mucosal membraneus tumors were administered with the tetramer form of DPA. In some cases, DPA, as a monomer, was used.

In most cases, the DPA monomer or oligomer was administered only once and without anesthesia or other special conditions.

The safety and efficacy of DPA oligomer treatment was assessed by evaluating the treated skin lesion appearance, local skin reaction, vital sign measurements, adverse events and concomitant medications taken by the patient. Inclusion criteria were as follows:

Sufficiently educated patients, suffering from various superficial skin pathologies, as described in detail hereinbelow, were enrolled. Patients included ambulatory patients older than 5 years old of both sexes and ambulatory female patients older than 18 years old without potential pregnancy or which are using an approved contraceptive method (intrauterine apparatus, contraceptive tablets of at least a menstrual cycle implants or diaphragm.

The following were excluded from the study:

Lactating or pregnant women; women with a potential pregnancy who are not using an approved method of contraception; Patients having serious advanced diseases, such as advanced cardiac conditions, final states of renal insufficiency, final states of neurological diseases; patients with a history of severe allergies of anaphylactic reactions to drugs or meals; patients with advanced psychiatry disorders; patients that consume alcohol or illicit drugs on a regular basis; and patients with advanced malignant skin lesions.

Study Protocol:

Patients were requested to provide complete and dermatological Clinical history. A dermatological evaluation of the lesion(s) was performed and clinically diagnosed. The clinical parameters of the afflicted tissue were measured and recorded. Biopsy was performed in some cases.

In patients suffering from multiple lesions, the number of lesions to be treated was determined.

All patients were treated by topically applying the tested solution locally (less than 0.01 cc), at the skin lesion area, using a micro-pipette. The skin lesion was photographs prior to treatment, immediately after the topical application of the tested solution, a week treatment and four weeks after treatment. Patients were thereafter tested during a time period of 2 years, for recurrence.

Clinical Results:

453 patients participated in this study, and a total of 2201 lesions were treated. Of these, 15 cases suffered from malignant tumors. Age distribution of the participants was as follows:

5-10 years old—20 patients; 11-20 years old—41 patients; 21-30 years old—62 patients; 41-40 years old—80 patients; 41-50—116 patients; 61-70 years old—98 patients; 71-80—31 patients; and 81-90—5 patients.

The following non-malignant lesions were treated:

| Lesion | No. (Total = 2149) |
| --- | --- |
| Actinic Keratosis | 237 |
| Condylomata | 150 |
| Epidermoid Cyst | 52 |
| Fibrolipomas | 56 |
| Hemangiomas | 12 |
| Kerato Acanthosis | 6 |
| Lentigo | 7 |
| Molluscum contagiosum | 148 |
| Mucosal Cysts | 3 |
| Neuro Fibromas | 3 |
| sebaceous Hyperplasia | 18 |
| Seborrheic keratoses | 358 |
| Several types of Fibromas | 560 |
| Several types of Nevus | 422 |
| Several types of Verrucas | 117 |

In about 98% of the above-indicated cases, the lesion was resolved, and no recurrence was observed two years following treatment. In the following cases recurrence was observed: Actinic keratosis (6 patients with 6 lesions); fibrolipoma (3 cases, 3 lesions); and plantar verrucas (5 cases, 13 lesions).

In patients having a malignant skin tumor, no recurrence of the neoplasm was observed during the indicated time period.

These results further emphasize the outstanding therapeutic activity of DPA or oligomers thereof, in treating a variety of skin pathologies.

Example 4

Devitalization of Malignant Tumors in Internal Tissues

General Protocols:

In one exemplary protocol, devitalization of primary tumor and/or tumor metastases is accomplished by direct intra-tumoral injection of DPA or oligomers thereof, as described herein, by direct vision at the time of surgery, or by ultrasound or CT-guided needle for devitalization of inoperable lesion or in preparation for surgical excision prior to or at the time of operation.

DPA, or an oligomer thereof, is mixed with radiopaque solution in order to control adequate saturation of lesions injected with the tested compound under fluoroscopy or CT monitoring.

Minimizing the risk of tumor cells spread in conjunction with surgical removal of malignant lesions is accomplished by topical application of the DPA or the oligomer thereof under direct vision around the excised lesion and lesion bed prior to complete removal of the lesion in order to eliminate spread of tumor cells during the excision process itself.

In another exemplary protocol, devitalization of tumor or tumor metastases is accomplished by injection of sub-toxic amount of DPA or an oligomer thereof into an afferent blood vessel or lymphatic circulation.

In another exemplary protocol, physical surgical removal of primary tumor and/or metastases is accompanied by anti-cancer immunization in order to minimize recurrence from minimal residual disease using one of the following methods:

(i) Systemic immunization by subcutaneous or intradermal administration of lysate of tumor cells modified by DPA or an oligomer therein, chemically or by viral antigens, in order to induce autoimmune-like reactivity against tumor cells [modified self];

(ii) Using tumor cell lysates by pulsing patient's own dendritic cells prepared ahead of time for immunization against residual tumor cells modified by DPA or an oligomer thereof;

(iii) Using tumor cell lysates for loading dendritic cells obtained from a family member sharing at least one MHC haplotype with a patient in order to induce alloreactive response against natural or modified tumor antigens; and (iv) Using the primary tumor or tumor metastases devitalized by DPA or an oligomer thereof, as an in situ tumor cell vaccine by intra-lesional injection of autologous or allogeneic dendritic cells without surgical excision in order to induce an immune response in situ against local residual viable tumor cells or against residual tumor cells elsewhere.

Taken together, a combination of local tumor devitalization, tumor excision following blocking surgically induced tumor spread and additional induction of anti-cancer immunotherapy by specific local or systemic immunization provide an optimal clinical method for improving the outcome of patients with solid tumors by optimizing elimination of all malignant cells in primary and metastatic cancer.

In Vivo Studies:

BALB/c mice and (BALB/cxC57BL/6)F1 mice (F1) are inoculated with a metastatic breast cancer 4T1 cell line into the lateral flank under the skin. This tumor grows locally and then metastases develop in the lungs and liver.

All mice are inoculated with 4T1 subcutaneously and divided into subgroups that are treated once a local tumor is visible as follows:

Group I: untreated controls.

Group II: controls treated with surgical removal of tumor.

Group III: mice treated with local injection of a DPA oligomer in incremental doses to check role of DPA on tumor growth and survival.

Group IV: mice treated with subtoxic doses x1, x2, x3 to test the effect of cumulative subtoxic doses of DPA on tumor growth and survival.

Group V: mice treated with DPA or subtoxic doses as in Group IV, prior to surgical excision of tumor.

Group VI: mice treated with subtoxic doses of DPA around the tumor bed prior to surgical excision.

Group VII: mice treated with surgical removal of tumor followed by immunotherapy with tumor cell vaccination or with alloreactive donor lymphocytes C57BL/6 stem cells into F1 recipients in comparison with recipients treated with tumor cell vaccine or alloreactive lymphocytes alone.

Group VIII: mice treated with intra-lesional inoculation of dendritic cells with and without prior devitalization with DPA.

Example 5

In Vivo Studies of Devitalization of a Primary Tumor by DPA or an Oligomer Thereof Prior to Surgical Removal Study Protocol:

Eight weeks old BALB/c mice were inoculated SC with $3.5 \times 10^6$ 4T1 (a model of metastatic breast cancer). On day +11, when tumors were visible under the skin, mice were divided into 3 groups, 16 mice per group, as follows:

Group 1 served as untreated control; Group 2 included mice treated with 20 microliter injections of DPA or an oligomer thereof into the primary tumor; Group 3 included mice treated with 20 microliter saline. One hour after treatment, mice were anesthetized and the primary tumor was surgically removed. At 3 weeks following tumor inoculation mice were sacrificed and lungs and spleens were tested for metastases and the weight of spleens was recorded.

Results

No cutaneous tumors were visible in mice treated with DPA or an oligomer thereof. In the untreated control Group 1, 5 mice died. In DPA-treated Group 2, no mice died. In group 3, 4 mice died.

Lung metastases were preset in all mice in the untreated control Group 1, in 2 mice of Group 2 and in 5 mice of Group 3.

Spleen weight was recorded. Spleen was enlarged and full of tumor metastases in all mice belonging to control Group 1 [average 0.477 grams]; less in mice of Group 3 [0.262 grams], and further less in mice belonging to group 2 [0.175 grams]. The difference between Groups 2 and 3 is significant [p=0.039] based on Levene's Test for Equality of Variances, and borderline significant [p=0.057] based on Multiple Comparison Graph.

The obtained results clearly show that treatment DPA or an oligomer thereof during a surgical procedure for removing a malignant tumor, is effective against the primary tumor. The treatment accomplished in situ within minutes, using reasonably well tolerated doses of a solution of DPA or an oligomer thereof. The obtained results demonstrate that devitalization by DPA or an oligomer thereof during surgical removal of tumors reduces the incidence of late remote metastases, which may be caused by systemic spread of tumor cells as a result of the trauma of surgery through damaged blood or lymphatic vessels.

Example 6

Ex-Vivo Treatment of Human's Meningioma

A subject suffering from meningioma, as shown using CTA 3D-MPR (see, FIG. 1A), underwent surgical removal of the tumor via LT Pterional craniotomy. On the next day, the excised meningioma was treated with DPA and/or oligomer thereof. The results are presented in FIGS. 1B-1D, and show excellent devitalization of the meningioma.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a skin tumor in a subject in need thereof, the method comprising administering to the subject a devitalizing effective amount of a tetramer of 2,2-dichloropropanoic acid or a pharmaceutical acceptable salt thereof, by locally administering the tetramer onto and/or into said skin tumor, wherein said tetramer comprises bonds between the monomeric units, said bonds being selected from the group consisting of ether bonds and ester bonds.

2. The method of claim 1, wherein said tetramer is selected from the group consisting of:

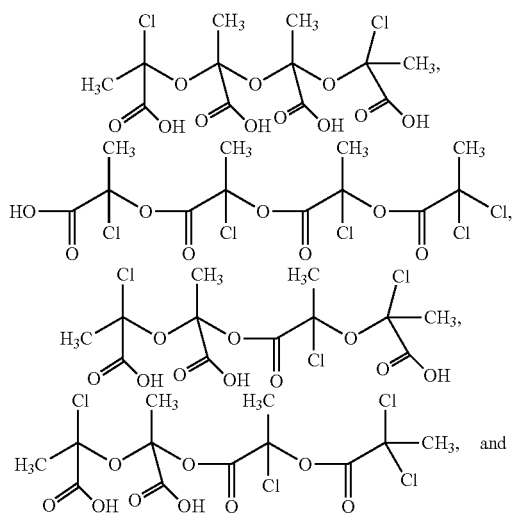

-continued

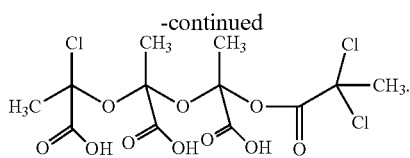

3. The method of claim 1, wherein said compound forms a part of a pharmaceutical composition which further comprises a pharmaceutically acceptable carrier.

4. The method of claim 3, wherein a concentration of said compound in said composition ranges from 20 weight percents to 100 weight percents of the total weight of said composition.

5. The method of claim 3, wherein a concentration of said compound in said composition ranges from 70 weight percents to 90 weight percents of the total weight of said composition.

6. The method of claim 3, wherein a devitalizing effective amount of said compound ranges from 0.001 ml to 5 ml of said composition per a skin tumor diameter of 1 cm.

7. The method of claim 1, wherein said skin tumor is selected from the group consisting of viral, benign, premalignant and malignant skin tumors.

8. The method of claim 1, further comprising surgically removing at least a portion of said skin tumor.

9. The method of claim 1, wherein said skin tumor is malignant, the method being for reducing or abolishing dissemination of malignant cells into blood or lymph vessels.

10. The method of claim 1, wherein said administering is effected topically.

11. A method of reducing or abolishing dissemination of malignant cells into a blood and/or lymph vessel of a subject having a malignant skin tumor and subjected to a surgical procedure for removing at least a portion of said malignant skin tumor, the method comprising administering to the subject, prior to, concomitant with or subsequent to the surgical procedure, a devitalizing effective amount of a tetramer of 2,2-dichloropropanoic acid or a pharmaceutical acceptable salt thereof, by locally administering the tetramer onto and/or into said skin tumor,
wherein said tetramer comprises bonds between the monomeric units, said bonds being selected from the group consisting of ether bonds and ester bonds.

12. The method of claim 11, wherein a devitalizing effective amount of said compound ranges from 0.001 ml to 5 ml of said composition per a skin tumor diameter of 1 cm.

13. The method of claim 11, wherein said skin tumor is a metastasizing malignant skin tumor.

14. The method of claim 11 wherein said administering is effected topically.

* * * * *